United States Patent
Singhal

(10) Patent No.: US 11,667,666 B2
(45) Date of Patent: Jun. 6, 2023

(54) METHODS AND COMPOSITIONS FOR TREATMENT OF CANCER

(71) Applicant: CFD Research Corporation, Huntsville, AL (US)

(72) Inventor: Anuj Singhal, Gurley, AL (US)

(73) Assignee: CFD RESEARCH CORPORATION, Huntsville, AL (US)

( * ) Notice: Subject to any disclaimer, the term of this patent is extended or adjusted under 35 U.S.C. 154(b) by 226 days.

(21) Appl. No.: 17/151,858

(22) Filed: Jan. 19, 2021

(65) Prior Publication Data

US 2021/0230212 A1    Jul. 29, 2021

Related U.S. Application Data

(60) Provisional application No. 62/963,338, filed on Jan. 20, 2020.

(51) Int. Cl.
| | |
|---|---|
| *A61K 45/06* | (2006.01) |
| *C07J 31/00* | (2006.01) |
| *C07C 59/72* | (2006.01) |
| *A61P 35/04* | (2006.01) |
| *C07D 409/04* | (2006.01) |

(52) U.S. Cl.
CPC .............. *C07J 31/006* (2013.01); *A61K 45/06* (2013.01); *A61P 35/04* (2018.01); *C07C 59/72* (2013.01); *C07D 409/04* (2013.01)

(58) Field of Classification Search
CPC ...................................................... A61P 35/04
See application file for complete search history.

(56) References Cited

PUBLICATIONS

Lopez, Biologics: Targets and Therapy 2016:10 139-148.*
Shah, J Clin Pharm Ther. 2019;44:6-2.*
Mészáros, Beáta et al. "The hEag1 K+ Channel Inhibitor Astemizole Stimulates Ca2+ Deposition in SaOS-2 and MG-63 Osteosarcoma Cultures." International journal of molecular sciences vol. 23,18 10533. Sep. 11, 2022, doi:10.3390/ijms231810533.
Hasanovic, Anida et al. "Astemizole Sensitizes Adrenocortical Carcinoma Cells to Doxorubicin by Inhibiting Patched Drug Efflux Activity." Biomedicines vol. 8,8 251. Jul. 29, 2020, doi:10.3390/biomedicines8080251.
Chávez-López, María de Guadalupe et al. "Eag1 Gene and Protein Expression in Human Retinoblastoma Tumors and its Regulation by pRb in HeLa Cells." Genes vol. 11,2 119 Jan. 21, 2020, doi:10.3390/genes11020119.
García-Quiroz, Janice et al. "Astemizole, an Inhibitor of ETHER-À-GO-GO-1 Potassium Channel, Increases the Activity of the Tyrosine Kinase Inhibitor Gefitinib in Breast Cancer Cells." Revista de investigacion clinica; organo del Hospital de Enfermedades de la Nutricion vol. 71,3 (2019): 186-194. doi:10.24875/RIC.18002840.
Laverdière, Isabelle et al. "Leukemic stem cell signatures identify novel therapeutics targeting acute myeloid leukemia." Blood cancer journal vol. 8,6 52. Jun. 6, 2018, doi:10.1038/s41408-018-0087-2.
Bernal-Ramos, Gloria et al. "Astemizole inhibits cell proliferation in human prostate tumorigenic cells expressing ether à-go-go-1 potassium channels." Cellular and molecular biology (Noisy-le-Grand, France) vol. 63,12 11-13. Dec. 17, 2017, doi:10.14715/cmb/2017.63.12.4.
Chávez-López, María de Guadalupe et al. "The combination astemizole-gefitinib as a potential therapy for human lung cancer." OncoTargets and therapy vol. 10 5795-5803. Dec. 6, 2017, doi:10.2147/OTT.S144506.
Sales, Thais Torquato et al. "Suppression of the Eag1 potassium channel sensitizes glioblastoma cells to injury caused by temozolomide." Oncology letters vol. 12,4 (2016): 2581-2589. doi:10.3892/ol.2016.4992.
Ellegaard, Anne-Marie et al. "Repurposing Cationic Amphiphilic Antihistamines for Cancer Treatment." EBioMedicine vol. 9 (2016): 130-139. doi: 10.1016/j.ebiom.2016.06.013.
García-Becerra, Rocío et al. "Calcitriol inhibits Ether-à go-go potassium channel expression and cell proliferation in human breast cancer cells." Experimental cell research vol. 316,3 (2010): 433-42. doi:10.1016/j.yexcr.2009.11.008.
Restrepo-Angulo, Iván et al. "Human EAG1 potassium channels in the epithelial-to-mesenchymal transition in lung cancer cells." Anticancer research vol. 31,4 (2011): 1265-70.
Garcia-Quiroz, Janice, and Javier Camacho. "Astemizole: an old anti-histamine as a new promising anti-cancer drug." Anti-cancer agents in medicinal chemistry vol. 11,3 (2011): 307-14. doi:10.2174/187152011795347513.

* cited by examiner

*Primary Examiner* — Nizal S Chandrakumar
(74) *Attorney, Agent, or Firm* — Thomas | Horstemeyer LLP

(57) ABSTRACT

In an aspect, the disclosure pertains to inhibitors of ANGPTL4; synthesis methods for making disclosed compounds; pharmaceutical compositions comprising disclosed compounds; methods of treating disorders of uncontrolled cellular proliferation, e.g., a cancer; and methods of treating a disease associated with an ANGPTL4 dysfunction using disclosed compounds and pharmaceutical compositions. This abstract is intended as a scanning tool for purposes of searching in the particular art and is not intended to be limiting of the present disclosure. This abstract is intended as a scanning tool for purposes of searching in the particular art and is not intended to be limiting of the present disclosure.

2 Claims, 7 Drawing Sheets

METHODS AND COMPOSITIONS FOR TREATMENT OF CANCER

CROSS-REFERENCE TO RELATED APPLICATIONS

This application claims the benefit of U.S. Provisional Application No. 62/963,338, filed on Jan. 20, 2020, which is incorporated herein by reference in its entirety.

BACKGROUND

Currently, chemotherapy and radiation therapy remain the most common methods for cancer treatment. These treatments were based on targeting proliferating cells rather than cancer cells only, which is also a factor in detrimental side effects from these treatments. Targeted therapy, a new generation of cancer treatment, targets cancer-specific changes of molecules and signaling pathways to inhibit cellular proliferation or induce cancer cell death, but with limited side effects on normal cells. Considerable effort has been made in finding the targets and the ways of affecting the targets inside the cells as a treatment, in particular for targets associated with difficult to treat cancers such as pancreatic cancer. For example, pancreatic ductal adenocarcinoma (PDAC) remains one of the most deadly cancers with an average survival of 3.5 months for non-resectable tumors. Gemcitabine is the primary prescribed chemotherapy drug for PDAC, but with only limited success.

Angiopoietin Like 4 (ANGPTL4) expression has been implicated in many cancer types and other diseases both as pathogenic and beneficial. It is known to occur in at least three isoforms, each with different functions. Previous work (Kirby, M. K., et al., 2016, *Molecular Oncology*, 10(8): 1169-1182), has shown varying gene expression levels for PDAC tumors correlating with survival outcomes. This study assessed RNA sequencing data from 119 patient tumor tissues, and 323 survival-correlated transcripts were identified. Further analysis revealed a 19-transcript predictive model for survival rates. In vitro patient tumor cell studies revealed a subset of these transcripts, which correlated with resistance to gemcitabine.

Despite advances in research directed towards improving outcomes with cancer, there is still a scarcity of compounds that are both potent, efficacious, and selective modulators of targets in cancer cells, such as ANGPTL4. These needs and other needs are satisfied by the present disclosure.

SUMMARY

In accordance with the purpose(s) of the disclosure, as embodied and broadly described herein, the disclosure, in an aspect, relates to compounds useful as inhibitors of angiopoietin-related protein 4 (ANGPTL4), and homologues thereof, methods of making same, pharmaceutical compositions comprising same, methods of treating disorders of uncontrolled cellular proliferation, such as a cancer, using same, and methods of treating a disorder associated with an ANGPTL4 dysfunction using same.

In an aspect, the disclosure pertains to compounds having a structure represented by a formula:

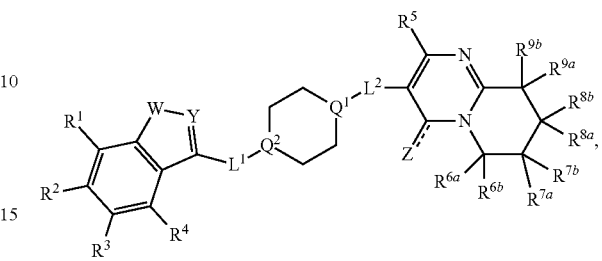

wherein $L^1$ is optionally present, and when present, $L^1$ is selected from —NH—, —CH$_2$—, —(CH$_2$)$_2$—, —(CH$_2$)$_3$—, —(CH$_2$)$_4$—, and —(CH$_2$)$_5$—; wherein $L^2$ is optionally present, and when present, $L^2$ is selected from —CH$_2$—, —(CH$_2$)$_2$—, —(CH$_2$)$_3$—, —(CH$_2$)$_4$—, and —(CH$_2$)$_5$—; wherein each of $Q^1$ and $Q^2$ is independently selected from —CH— and N, provided that $Q^2$ and $L^1$ are not simultaneously N; wherein W is selected from —O—, —S—, —CH$_2$—, or —NH—; wherein Y is selected from —CH— or N; wherein Z is selected from O, S, halogen, hydroxyl, cyano, —NH$_2$, and —SF$_5$, and wherein the dashed line represents an optional bond as required to maintain standard valency; wherein each of $R^1$, $R^2$, $R^3$, and $R^4$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; wherein $R^5$ is selected from hydrogen and C1-C6 alkyl; and wherein each of $R^{6a}$, $R^{6b}$, $R^{7a}$, $R^{7b}$, $R^{8a}$, $R^{8b}$, $R^{9a}$, and $R^{9b}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; or a pharmaceutically acceptable salt thereof; provided that the compound is not:

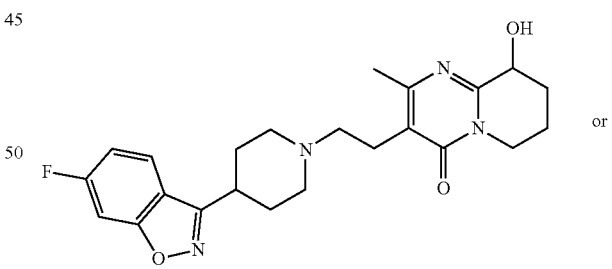

or

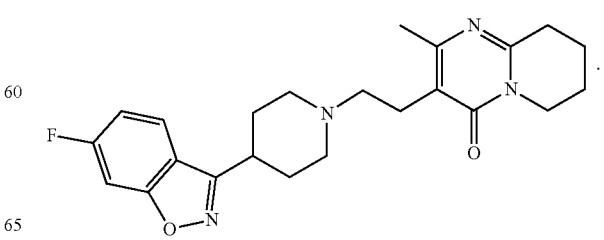

In an aspect, the disclosure pertains to compounds having a structure represented by a formula:

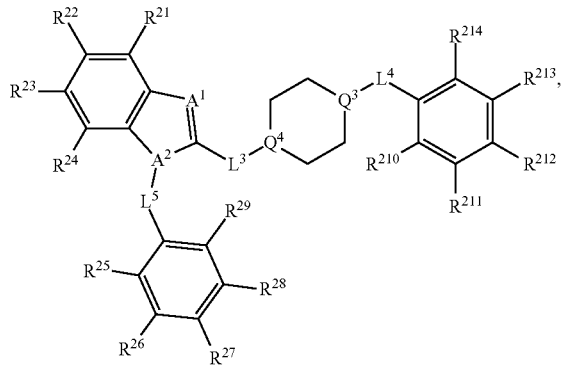

wherein L³ is optionally present, and when present, L³ is selected from —NH—, —CH₂—, —(CH₂)₂—, —(CH₂)₃—, —(CH₂)₄—, and —(CH₂)₅—; wherein L⁴ is optionally present, and when present, L⁴ is selected from —CH₂—, —(CH₂)₂—, —(CH₂)₃—, —(CH₂)₄—, and —(CH₂)₅—; wherein L⁵ is optionally present, and when present, L⁵ is selected from —CH₂—, —(CH₂)₂—, —(CH₂)₃—, —(CH₂)₄—, and —(CH₂)₅—; wherein each of Q³ and Q⁴ is independently selected from —CH— and N, provided that Q⁴ and L³ are not simultaneously N; wherein each of A¹ and A² is independently selected from —N— or —CH—; wherein each of R²¹, R²², R²³, and R²⁴ is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; wherein each of R²⁵, R²⁶, R²⁷, R²⁸, and R²⁹ is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; and wherein each of R²¹⁰, R²¹¹, R²¹², R²¹³, and R²¹⁴ is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; or a pharmaceutically acceptable salt thereof; provided that the compound is not:

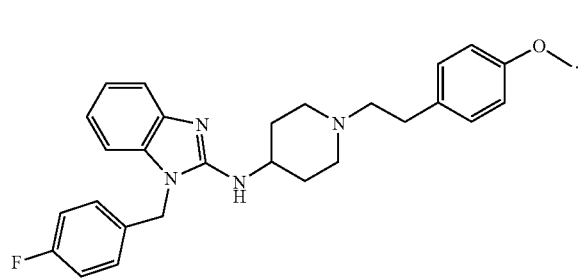 [SMILES: COc1ccc(CCN2CCC(Nc3nc4ccccc4n3Cc3ccc(F)cc3)CC2)cc1]

In an aspect, the disclosure pertains to compounds having a structure represented by a formula:

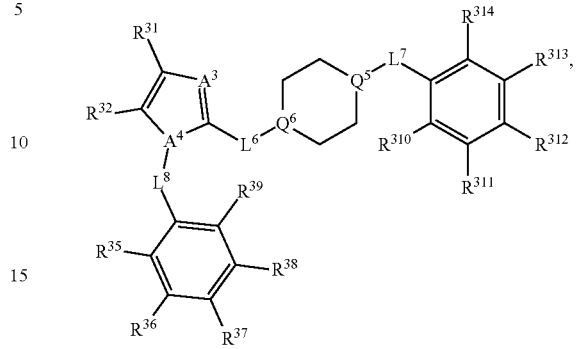

wherein L⁶ is optionally present, and when present, L⁶ is selected from —NH—, —CH₂—, —(CH₂)₂—, —(CH₂)₃—, —(CH₂)₄—, and —(CH₂)₅—; wherein L⁷ is optionally present, and when present, L⁷ is selected from —CH₂—, —(CH₂)₂—, —(CH₂)₃—, —(CH₂)₄—, and —(CH₂)₅—; wherein L⁸ is optionally present, and when present, L⁸ is selected from —CH₂—, —(CH₂)₂—, —(CH₂)₃—, —(CH₂)₄—, and —(CH₂)₅—; wherein each of Q⁵ and Q⁶ is independently selected from —CH— and N, provided that Q⁶ and L⁶ are not simultaneously N; wherein each of A³ and A⁴ is independently selected from —N— or —CH—; wherein each of R³¹ and R³² is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; wherein each of R³⁵, R³⁶, R³⁷, R³⁸, and R³⁹ is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; and wherein each of R³¹⁰, R³¹¹, R³¹², R³¹³, and R³¹⁴ is independently selected from hydrogen, halogen, cyano, hydroxyl, —NH₂, —SF₅, —O(C1-C6 alkyl), —S(C1-C6 alkyl), C1-C6 haloalkyl, and C1-C6 hydroxyalkyl; or a pharmaceutically acceptable salt thereof.

In an aspect, the disclosure pertains to pharmaceutical compositions comprising a therapeutically effective amount of one or more disclosed compounds, or a compound having a structure represented by a formula:

-continued

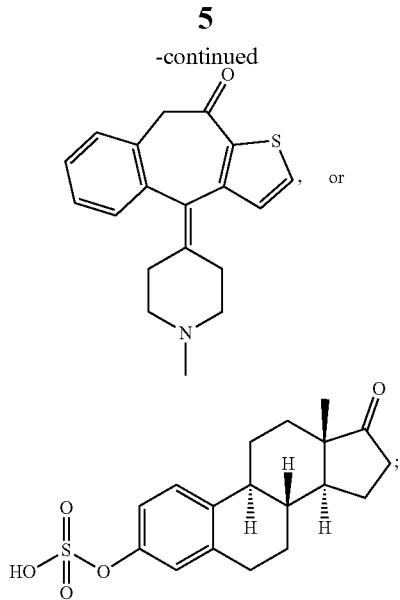

or pharmaceutically acceptable salt thereof, and a pharmaceutically acceptable carrier.

In an aspect, the disclosure pertains to methods for the treatment of a disorder of uncontrolled cellular proliferation associated with an ANGPTL4 dysfunction in a mammal comprising the step of administering to the mammal a therapeutically effective amount of at least one disclosed compound, or pharmaceutically acceptable thereof.

In an aspect, the disclosure pertains to methods for modulation of ANGPTL4 activity in a mammal comprising the step of administering to the mammal a therapeutically effective amount of at least one disclosed compound, or pharmaceutically acceptable salt thereof.

In an aspect, the disclosure pertains to methods for modulation of ANGPTL4 activity in at least one cell, comprising the step of contacting the cell with an effective amount of at least one disclosed compound, or pharmaceutically acceptable salt thereof.

In an aspect, the disclosure pertains to uses of a disclosed compound, or a pharmaceutically acceptable salt thereof.

In an aspect, the disclosure pertains to uses of a disclosed compound, or a pharmaceutically acceptable salt thereof, in the manufacture of a medicament for the treatment of a disorder associated with an ANGPTL4 dysfunction in a mammal.

In an aspect, the disclosure pertains to methods for the manufacture of a medicament to modulate ANGPTL4 activity in a mammal comprising combining at least one disclosed compound, or a pharmaceutically acceptable salt thereof, with a pharmaceutically acceptable carrier or diluent.

In an aspect, the disclosure pertains to kits comprising at least one disclosed compound, or a pharmaceutically acceptable salt thereof, and at least one of: (a) at least one agent known to increase ANGPTL4 activity; (b) at least one agent known to decrease ANGPTL4 activity; (c) at least one agent known to treat a disorder associated with ANGPTL4 activity; (d) instructions for treating a disorder associated with ANGPTL4 activity; (e) instructions for treating a disorder associated with ANGPTL4 activity; or (f) instructions for administering the compound in connection with treating a disorder of uncontrolled cellular proliferation.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

Figure 1:
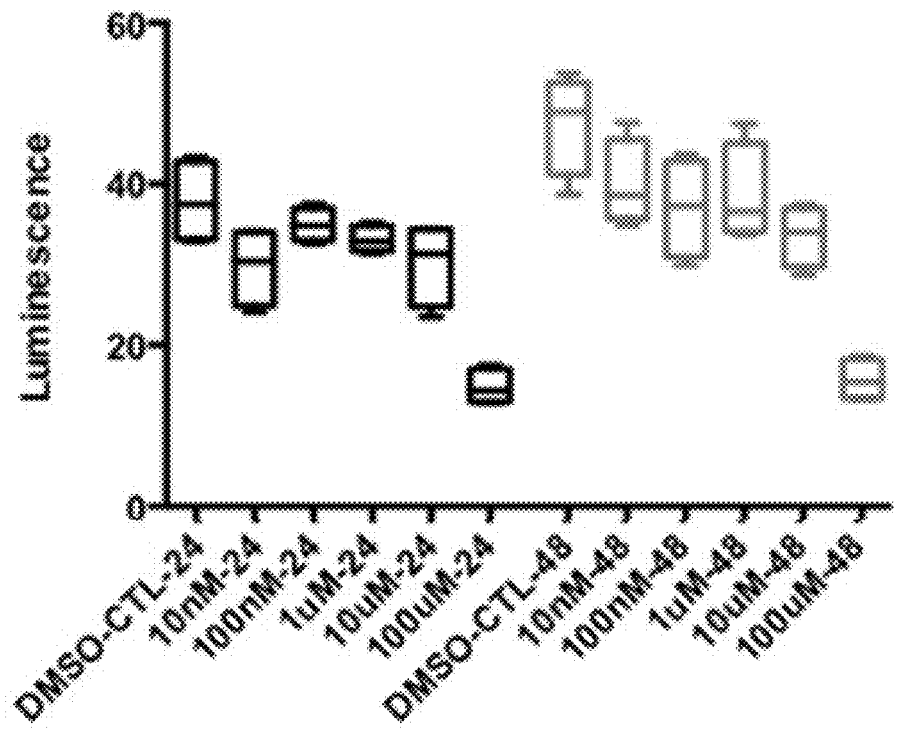
FIG. 1 shows representative data for inhibition of in vitro cellular proliferation using PANC-1 cells exposed to a representative disclosed compound, paliperidone.
Figure 2:
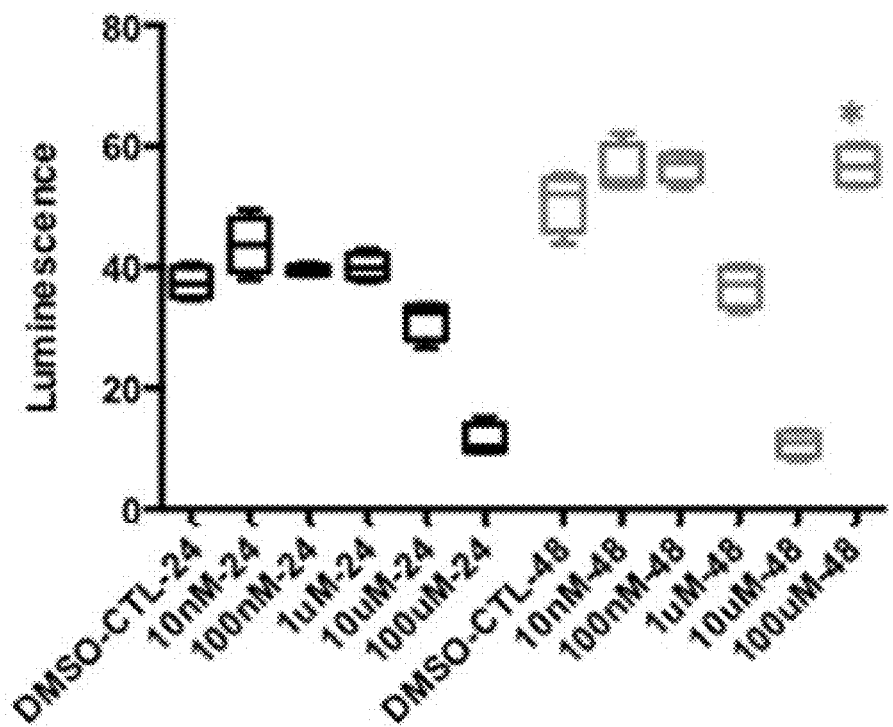
FIG. 2 shows representative data for inhibition of in vitro cellular proliferation using PANC-1 cells exposed to a representative disclosed compound, risperidone.
Figure 3:
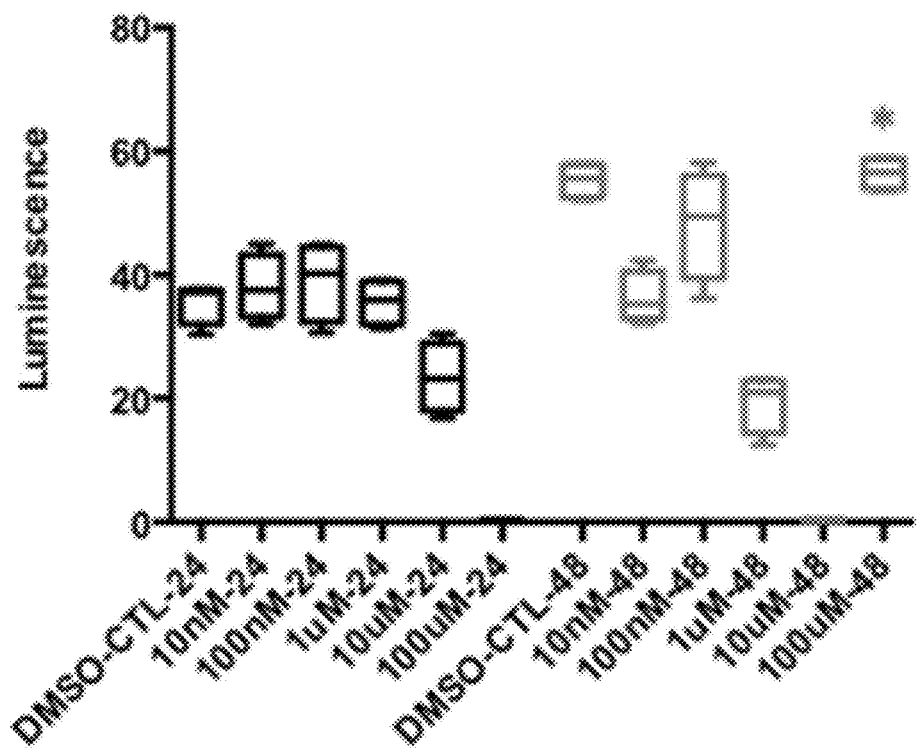
FIG. 3 shows representative data for inhibition of in vitro cellular proliferation using PANC-1 cells exposed to a representative disclosed compound, astemizole.
Figure 4:
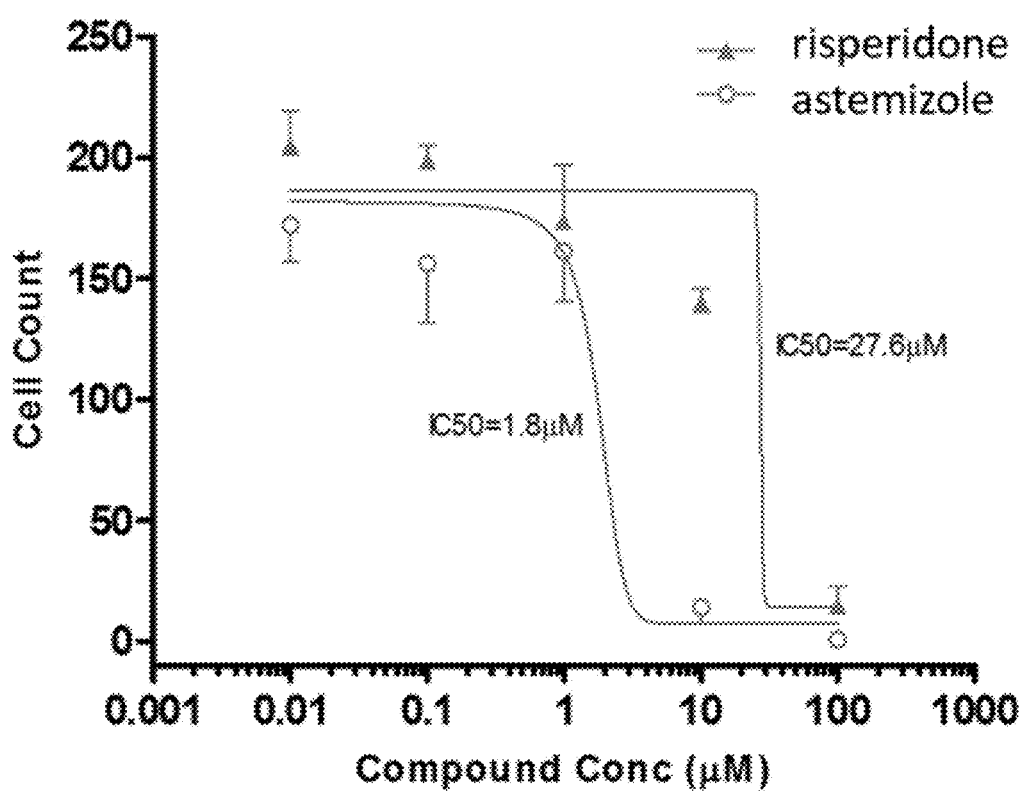
FIG. 4 shows representative data used to determine $IC_{50}$ for inhibition of cellular proliferation for PANC-1 cells treated with the indicated compound.
Figure 5:
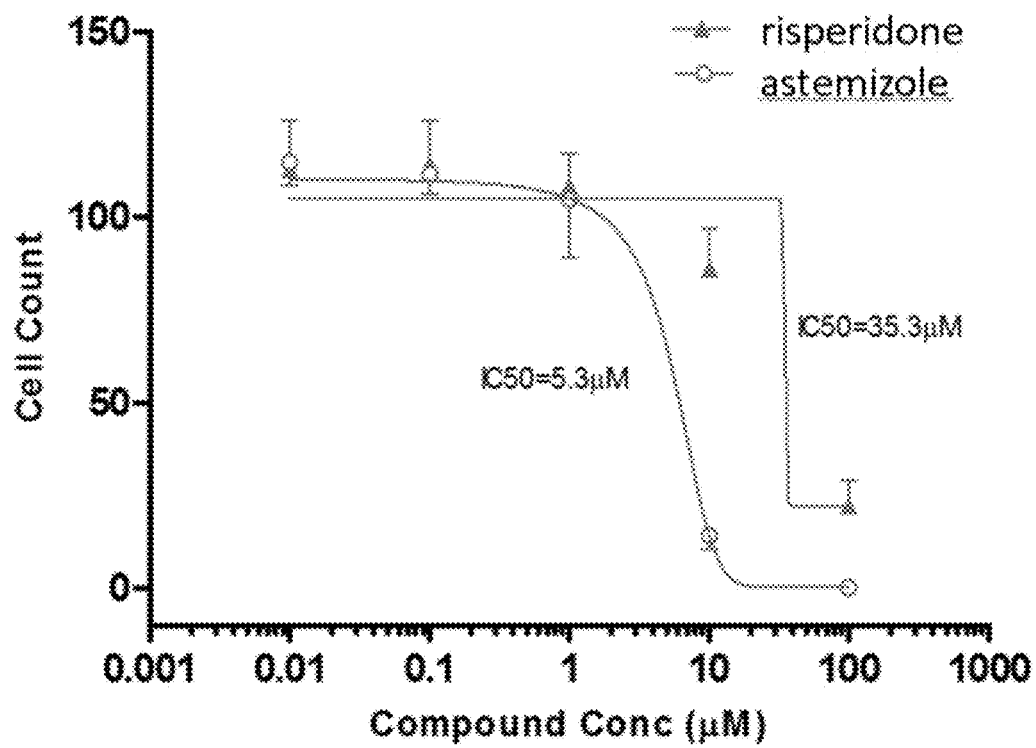
FIG. 5 shows representative data used to determine $IC_{50}$ for inhibition of cellular proliferation for ASPC 1 cells treated with the indicated compound.
Figure 6:
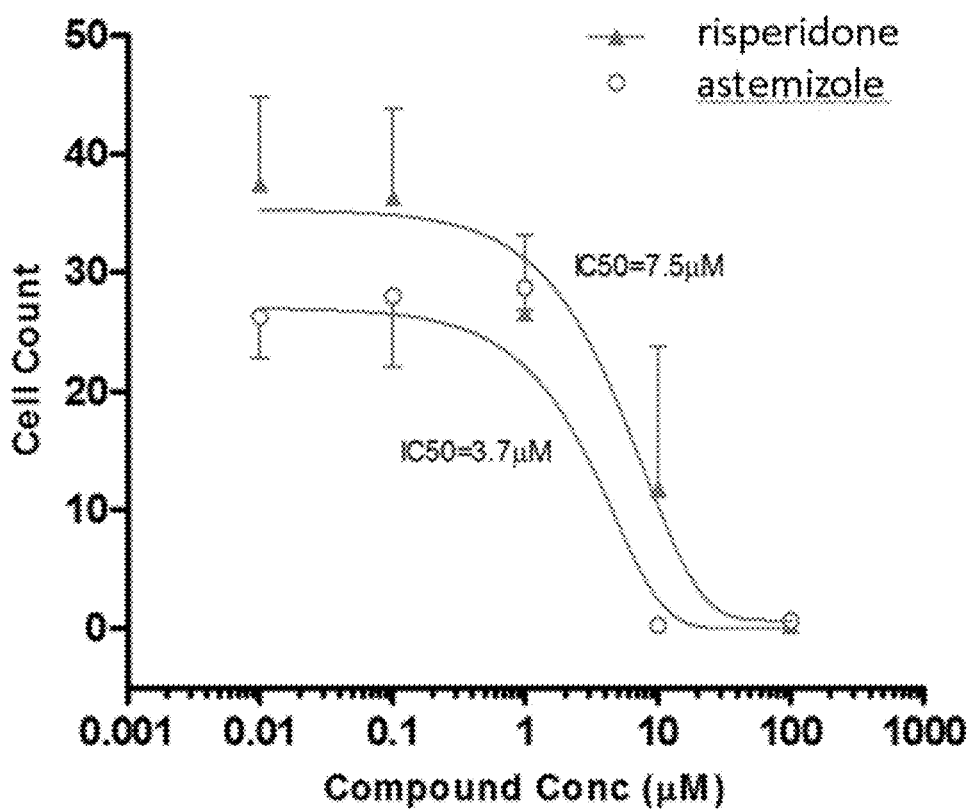
FIG. 6 shows representative data used to determine $IC_{50}$ for inhibition of cellular proliferation for BXPC-3 cells treated with the indicated compound.
Figure 7:
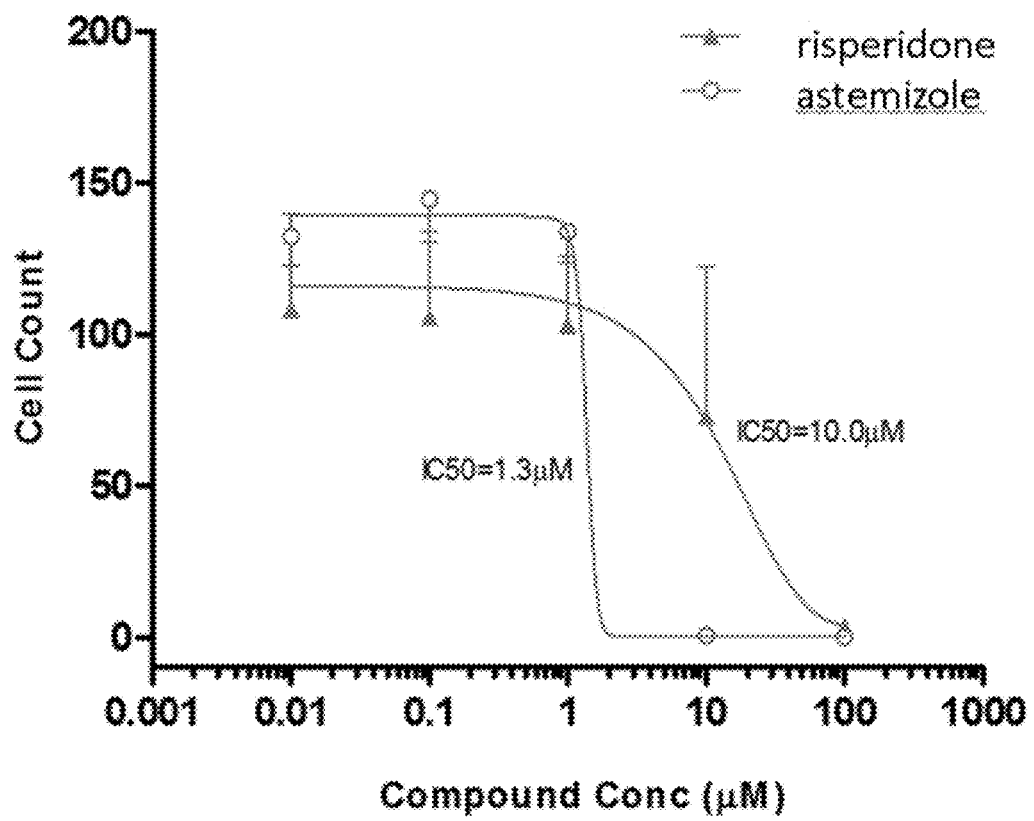
FIG. 7 shows representative data used to determine $IC_{50}$ for inhibition of cellular proliferation for MIA-PaCa-2 cells treated with the indicated compound.
Figure 8:
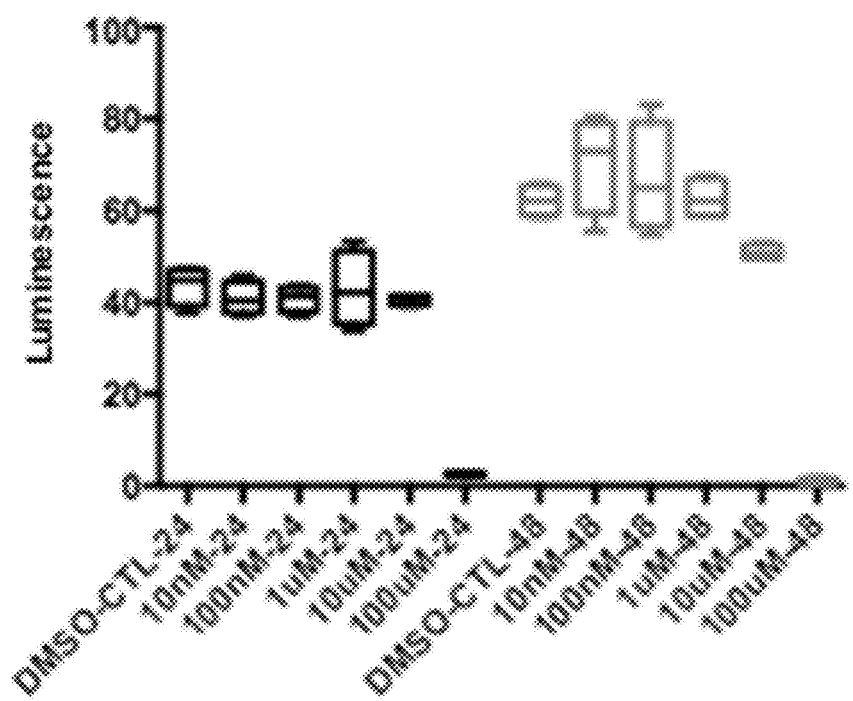
FIG. 8 shows representative data for inhibition of in vitro cellular proliferation using PANC-1 cells exposed to a representative disclosed compound, adapalene.
Figure 9:
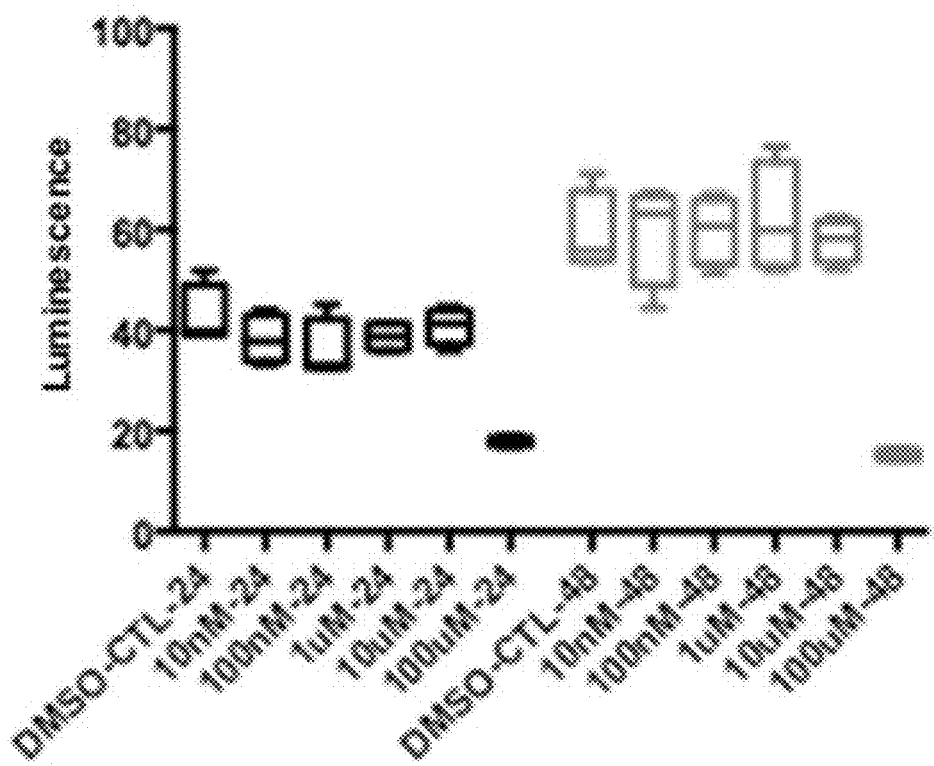
FIG. 9 shows representative data for inhibition of in vitro cellular proliferation using PANC-1 cells exposed to a representative disclosed compound, ketotifen.
Figure 10:
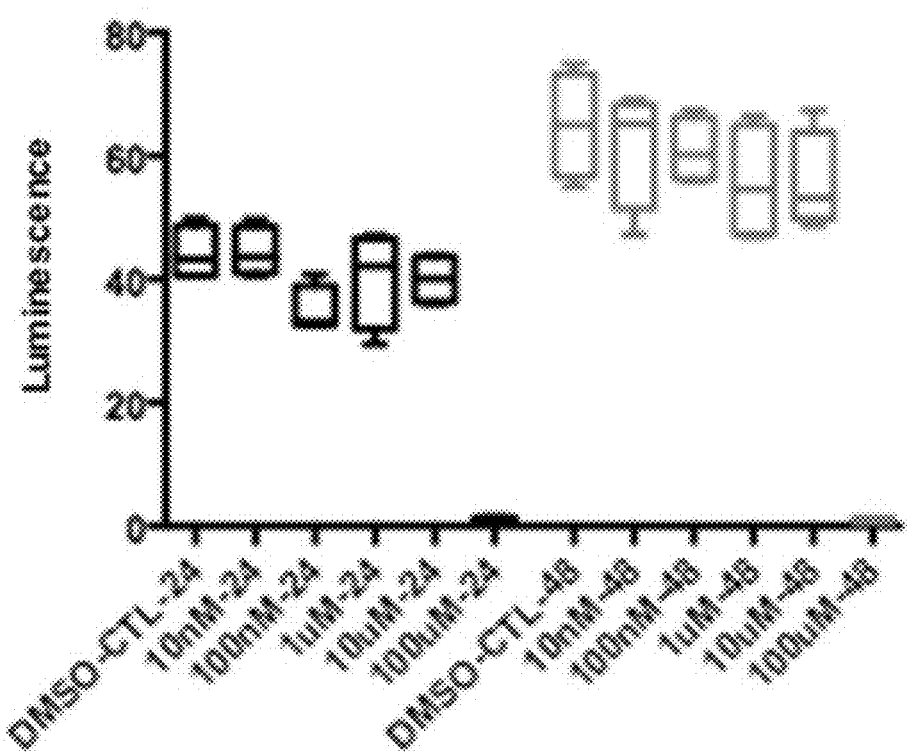
FIG. 10 shows representative data for inhibition of in vitro cellular proliferation using PANC-1 cells exposed to a representative disclosed compound, estropipate.
Figure 11A:
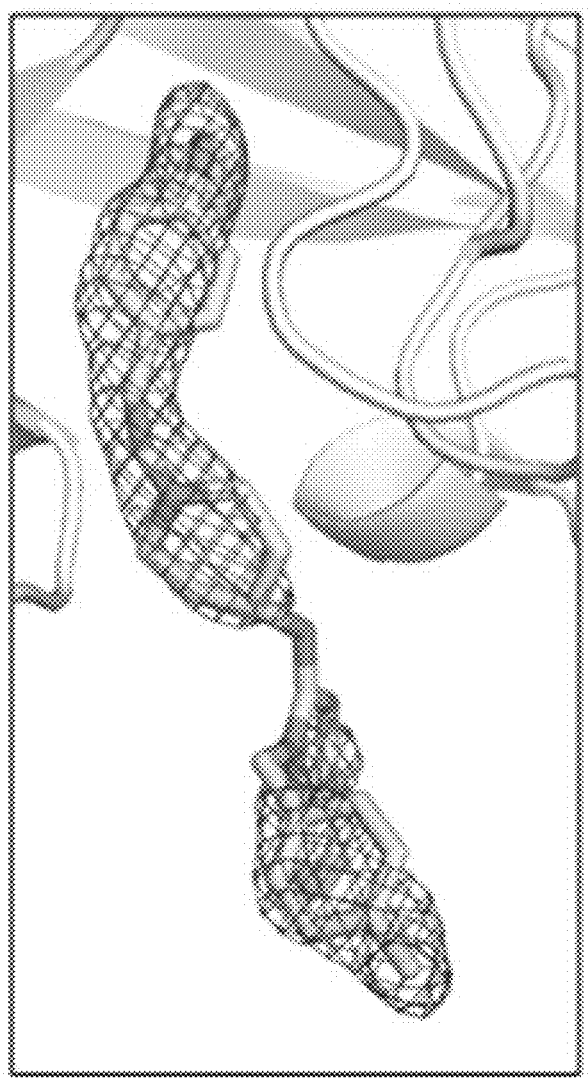
FIGS. 11A and 11B show a representative model for binding of astemizole within a pocket of ANGPTL4 within the C-terminal portion of the protein.
Figure 11B:
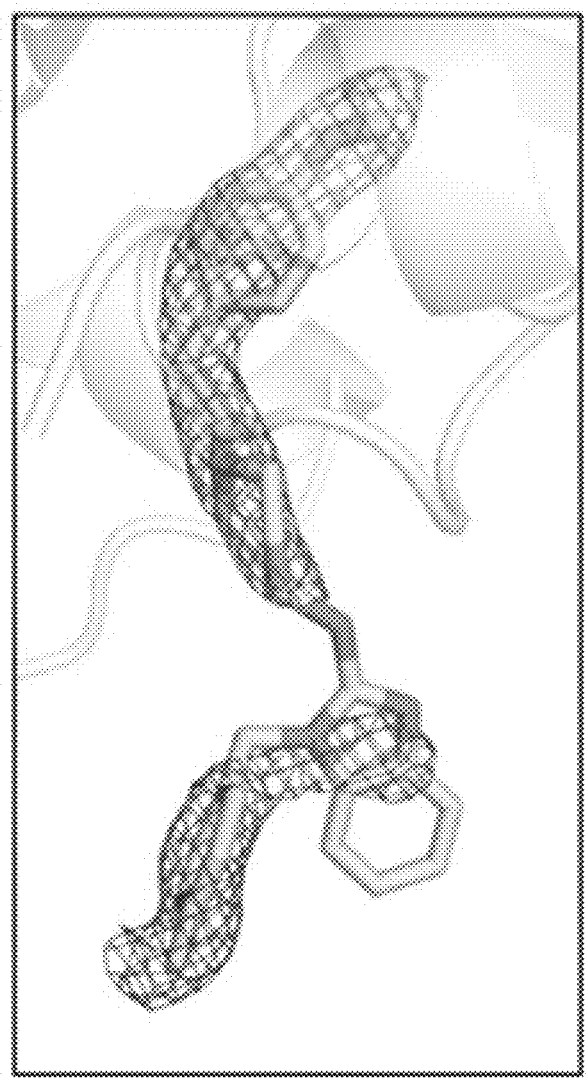

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description

DESCRIPTION

The present disclosure can be understood more readily by reference to the following detailed description of the disclosure and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw® (PerkinElmer, Inc., Waltham, Massachussetts).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used herein, "ANGPTL4," "Angiopoietin-related protein 4," or "Angiopoietin Like 4" refer to a protein encoded by a human gene located at chromosomal location 19p13.2. The terms are also inclusive of protein homologues of the human protein. The human gene encodes three isoforms which are generated by alternative mRNA splice variants. The three protein isoforms are designated in the UniProtKB/Swiss-Prot database with the identifiers: Q9BY76-1, Q9BY76-2, and Q9BY76-3. The canonical protein sequence is associated with UniProtKB/Swiss-Prot database with the identifiers, Q9BY76-1, which is a 406 amino acid protein with a molecular weight of 45,214 kD. The ANGPTL4 protein is a glycosylated, secreted protein containing a C-terminal fibrinogen domain. The secreted protein circulates as a homooligomer.

The homooligomer undergoes proteolytic processing to release its carboxyl fibrinogen-like domain, which circulates as a monomer. The C-terminal domain may be proteolytically-cleaved from the full-length secreted protein in vivo. The C-terminal domain is referred to as cANGPTL4. The natural cleavage site in vivo can occur between amino acids 162-229 of the canonical sequence.

As used herein, the term "cANGPTL4" refers to a C-terminal fragment of the canonical ANGPTL4 human protein sequence beginning at any amino acid position between 162-229, or homologues thereof. In an aspect, the terminal fragment, cANGPTL4, comprises amino acid residues 179-406 of the canonical ANGPTL4 human protein sequence, or homologues thereof. In an aspect, the terminal fragment, cANGPTL4, comprises amino acid residues 184-406 of the canonical ANGPTL4 human protein sequence, or homologues thereof. Unless specified otherwise, the use of "ANGPTL4" is inclusive of reference to both ANGPTL4 and cANGPTL4.

As used herein, the term "ANGPTL4 modulator" or "modulator of ANGPTL4" refers to a compound or agent that directly or indirectly modulates the activity of ANGPTL4, as an isolated protein, in a cell or in an animal, in particular a mammal, for example a human. For example, an ANGPTL4 modulator can alter the basal activity level of isolated ANGPTL4 in vitro or the activity of ANGPTL4 in a cell, in vivo or in vitro. In an aspect, an ANGPTL4 modulator can inhibit the activity of ANGPTL4 in a cell. The cell can be a mammalian cell line transfected with human ANGPTL4. The cell can be a mammalian cell line transfected with a rodent, e.g., rat, ANGPTL4. The cell can be a mammalian cell line transfected with a mammalian ANGPTL4. The cell can be a cancer cell-line such as PANC-1, ASPC 1, BXPC-3, or MIA-PaCa-2 cells.

As used herein, the term "modulation of ANGPTL4 activity" refers to modulation of either ANGPTL4 or cANGPTL4 activity or both, unless otherwise specified. Modulation of activity, as understood herein, is altering the activity of ANGPTL4 from a baseline level of activity, e.g., inhibition of a baseline or basal activity level. Accordingly, in some aspects, modulation can be inhibition of ANGPTL4 activity. The modulation, for example, inhibition, of ANGPTL4 activity in a cell can result in cell death or inhibition of cellular proliferation.

As used herein, the term "subject" can be a vertebrate, such as a mammal, a fish, a bird, a reptile, or an amphibian. Thus, the subject of the herein disclosed methods can be a human, nonhuman primate, horse, pig, rabbit, dog, sheep, goat, cow, cat, guinea pig or rodent. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). The term does not denote a particular age or sex. Thus, adult and newborn subjects, as well as fetuses, whether male or female, are intended to be covered. In an aspect, the subject is a mammal. A patient refers to a subject afflicted with a disease or disorder. The term "patient" includes human and veterinary subjects. In an aspect of a disclosed method, the subject has been diagnosed with a need for treatment of one or more disorders of uncontrolled cellular proliferation associated with an ANGPTL4 dysfunction, e.g., aberrant expression of ANGPTL4. In an aspect of a disclosed method, the subject has been diagnosed with a need for modulation of ANGPTL4 activity. In an aspect of a disclosed method, the subject has been diagnosed with a disorder of uncontrolled cellular proliferation, e.g. cancer. In an aspect of a disclosed method, the subject has been identified with a disorder treatable by modulation of ANGPTL4 activity. In an aspect, a subject can be treated prophylactically with a compound or composition disclosed herein. In an aspect, the subject is a mammal such as a primate. In an aspect, the subject is a human.

As used herein, the term "treatment" refers to the medical management of a patient with the intent to cure, ameliorate, stabilize, or prevent a disease, pathological condition, or disorder. Treatment includes active treatment, that is, treatment directed specifically toward the improvement of the health of a subject with a disease, pathological condition, or disorder, and also includes causal treatment, that is, treatment directed toward removal of the cause of the associated disease, pathological condition, or disorder. In addition, treatment includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, treatment includes any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of ANGPTL4 activity" means having been subjected to a physical examination by a person of skill, for example, a physician, and found to have a condition that can be diagnosed or treated by a compound or composition that can modulate ANGPTL4 activity.

As used herein, the phrase "identified to be in need of treatment for a disorder," or the like, refers to selection of a subject based upon need for treatment of the disorder. For example, a subject can be identified as having a need for treatment of a disorder (e.g., a disorder related to ANGPTL4 activity) based upon an earlier diagnosis by a person of skill and thereafter subjected to treatment for the disorder. It is contemplated that the identification can, in an aspect, be performed by a person different from the person making the diagnosis. It is also contemplated, in an aspect, that the administration can be performed by one who subsequently performed the administration.

As used herein, the terms "administering" and "administration" refer to any method or route of administration of a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target (e.g. ANGPTL4), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; anti spasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% modulation of a biological process, or component of a process. For example, $IC_{50}$ refers to the half maximal (50%) inhibitory concentration (IC) of a substance as determined in a suitable assay. For example, an $IC_{50}$ for ANGPTL4 can be determined in an in vitro using purified or isolated ANGPTL4, or alternatively in an in vitro cell-based assay system. Frequently, assays, including suitable assays for ANGPTL4 modulation, make use of a suitable cell-line, e.g. a cell line that either expresses endogenously a target of interest, has been transfected with a suitable expression vector that directs expression of a recombinant form of the target such as ANGPTL4, or is a cell-line derived from a cancer that can be associated with ANGPTL4 over-expression. For example, the $IC_{50}$ for ANGPTL4 can be determined using cell-lines such as PANC-1, ASPC 1, BXPC-3, or MIA-PaCa-2 cells, and determined the effect of a compound on cell proliferation using an assay for cellular proliferation, e.g., a luminescent-based assay such as the Cell Titer-Glo® (Promega Corporation, Madison, Wis.).

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and which structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1\text{-}(OA^2)_a\text{-}OA^3$, where "a" is an integer of from 1 to 200 and $A^1$, $A^2$, and $A^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $—NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula $—NH(\text{-alkyl})$ or $—N(\text{-alkyl})_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "nitro" as used herein is represented by the formula $—NO_2$.

The term "nitrile" or "cyano" as used herein is represented by the formula $—CN$.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula $—SH$.

"$A^1$," "$A^2$," . . . "$A^n$"; "$L^1$," "$L^2$," . . . "$L^n$"; and "$R^1$," "$R^2$," . . . "$R^n$"; and the like, where n is an integer, are used herein as generic symbols to represent various specific substituents and can, independently, possess one or more of the groups listed above as defined within this disclosure. These symbols can be any substituent, not limited to those disclosed herein, and when they are defined to be certain substituents in one instance, they can, in another instance, be defined as some other substituents. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In an aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

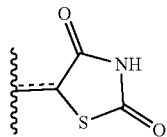

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In an aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. Disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$ isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

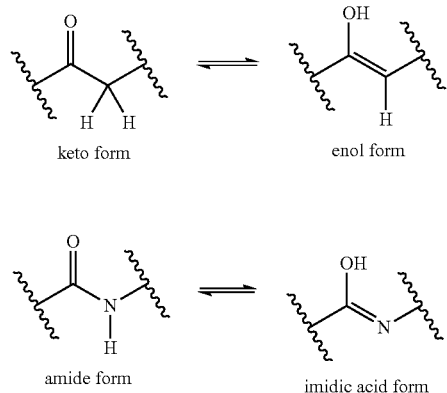

keto form    enol form amide form    imidic acid form

Likewise, amides with an N-hydrogen can exist in an equilibrium of the amide form and the imidic acid form. Unless stated to the contrary, the disclosure includes all such possible tautomers.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

In some aspects, a structure of a compound can be represented by a formula:

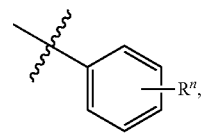

which is understood to be equivalent to a formula:

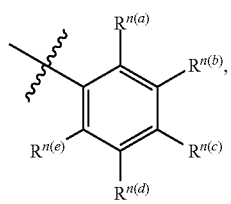

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

As used herein, "adapalene" refers to a compound having a structure represented by the formula:

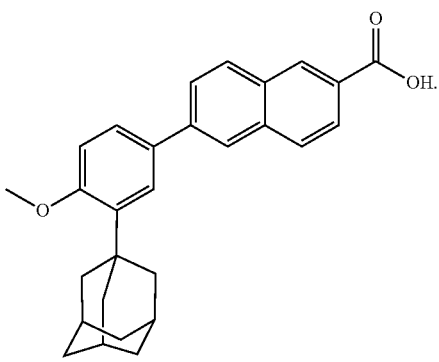 [SMILES: COc1ccc(-c2ccc3cc(C(=O)O)ccc3c2)cc1C12CC3CC(CC(C3)C1)C2]

As used herein, "astemizole" refers to a compound having a structure represented by the formula:

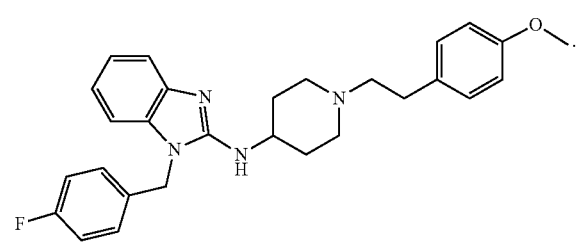 [SMILES: COc1ccc(CCN2CCC(Nc3nc4ccccc4n3Cc3ccc(F)cc3)CC2)cc1]

As used herein, "estropipate" refers to a compound having a structure represented by the formula:

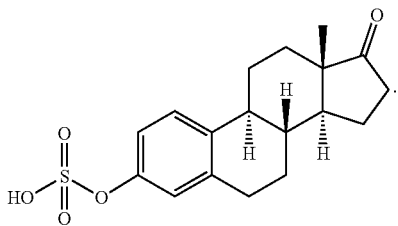

As used herein, "ketotifen" refers to a compound having a structure represented by the formula:

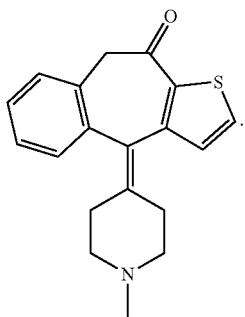 [SMILES: CN1CCC(=C2c3ccccc3CC(=O)c3sccc32)CC1]

As used herein, "paliperidone" refers to a compound having a structure represented by the formula:

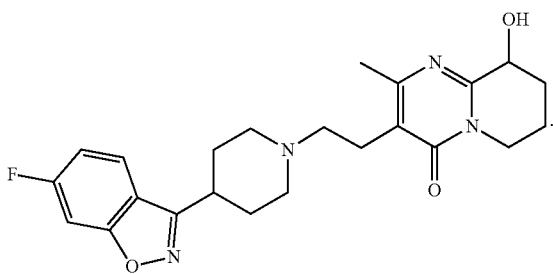 [SMILES: Cc1nc2n(c(=O)c1CCN1CCC(c3noc4cc(F)ccc34)CC1)CCCC2O]

As used herein, "risperidone" refers to a compound having a structure represented by the formula:

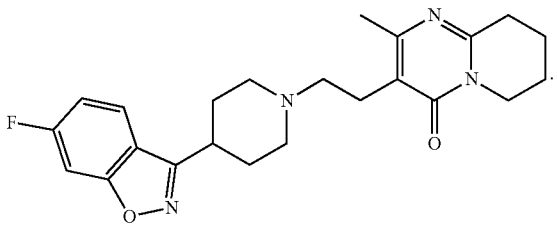 [SMILES: Cc1nc2n(c(=O)c1CCN1CCC(c3noc4cc(F)ccc34)CC1)CCCC2]

Certain materials, compounds, compositions, and components disclosed herein can be obtained commercially or readily synthesized using techniques generally known to those of skill in the art. For example, the starting materials and reagents used in preparing disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

In an aspect, the disclosure pertains to compounds useful as inhibitors of ANGPTL4. In an aspect, the compounds of the disclosure are useful in the treatment of disorders of uncontrolled cellular proliferation, e.g., a cancer, associated with an ANGPTL4 dysfunction, e.g., aberrant expression levels of ANGPTL4, and other diseases in which an ANGPTL4 dysfunction is involved.

It is contemplated that each disclosed derivative can be optionally further substituted. It is also contemplated that any one or more derivative can be optionally omitted from the disclosure. It is understood that a disclosed compound can be provided by the disclosed methods. It is also understood that disclosed compounds can be employed in the disclosed methods of using.

In an aspect, the disclosure pertains to a compound having a structure represented by a formula:

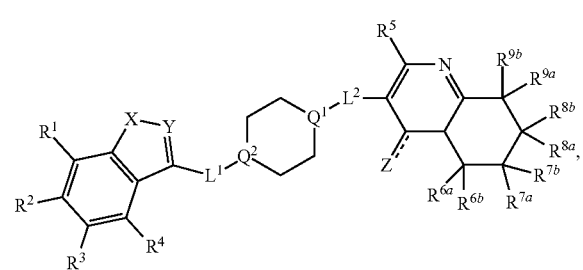

wherein L$^1$ is optionally present, and when present, L$^1$ is selected from —NH—, —CH$_2$—, —(CH$_2$)$_2$—, —(CH$_2$)$_3$—, —(CH$_2$)$_4$—, and —(CH$_2$)$_5$—; wherein L$^2$ is optionally present, and when present, L$^2$ is selected from —CH$_2$—, —(CH$_2$)$_2$—, —(CH$_2$)$_3$—, —(CH$_2$)$_4$—, and —(CH$_2$)$_5$—; wherein each of Q$^1$ and Q$^2$ is independently selected from —CH— and N, provided that Q$^2$ and L$^1$ are not simultaneously N; wherein W is selected from —O—, —S—, —CH$_2$—, or —NH—; wherein Y is selected from —CH— or N; wherein Z is selected from O, S, halogen, hydroxyl, cyano, —NH$_2$, and —SF$_5$, and wherein the dashed line represents an optional bond as required to maintain standard valency; wherein each of R$^1$, R$^2$, R$^3$, and R$^4$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; wherein R$^5$ is selected from hydrogen and C1-C6 alkyl; and wherein each of R$^{6a}$, R$^{6b}$, R$^{7a}$, R$^{7b}$, R$^{8a}$, R$^{8b}$, R$^{9a}$, and R$^{9b}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; or a pharmaceutically acceptable salt thereof; provided that the compound is not:

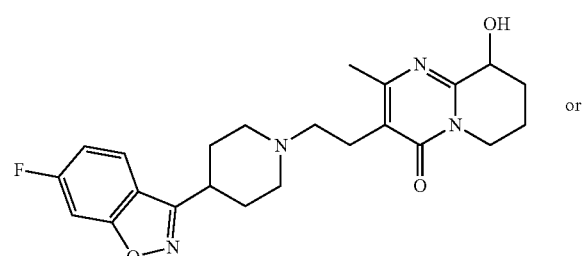

or

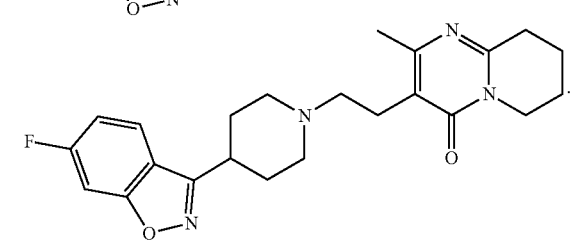

In an aspect, the disclosure pertains to a compound having a structure represented by a formula:

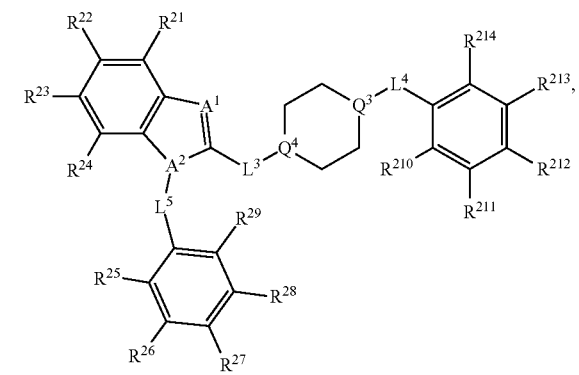

wherein L$^3$ is optionally present, and when present, L$^3$ is selected from —NH—, —CH$_2$—, —(CH$_2$)$_2$—, —(CH$_2$)$_3$—, —(CH$_2$)$_4$—, and —(CH$_2$)$_5$—; wherein L$^4$ is optionally present, and when present, L$^4$ is selected from —CH$_2$—, —(CH$_2$)$_2$—, —(CH$_2$)$_3$—, —(CH$_2$)$_4$—, and —(CH$_2$)$_5$—; wherein L$^5$ is optionally present, and when present, L$^5$ is selected from —CH$_2$—, —(CH$_2$)$_2$—, —(CH$_2$)$_3$—, —(CH$_2$)$_4$—, and —(CH$_2$)$_5$—; wherein each of Q$^3$ and Q$^4$ is independently selected from —CH— and N, provided that Q$^4$ and L$^3$ are not simultaneously N; wherein each of A$^1$ and A$^2$ is independently selected from —N— or —CH—; wherein each of R$^{21}$, R$^{22}$, R$^{23}$, and R$^{24}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; wherein each of R$^{25}$, R$^{26}$, R$^{27}$, R$^{28}$, and R$^{29}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; and wherein each of R$^{210}$, R$^{211}$, R$^{212}$, R$^{213}$, and R$^{214}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; or a pharmaceutically acceptable salt thereof; provided that the compound is not:

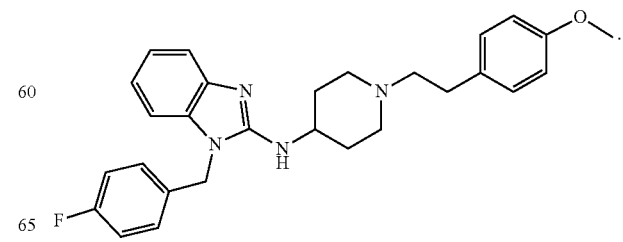

In an aspect, the disclosure pertains to a compound having a structure represented by a formula:

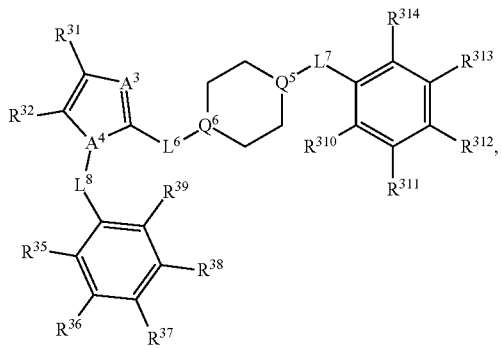

wherein $L^6$ is optionally present, and when present, $L^6$ is selected from —NH—, —CH$_2$—, —(CH$_2$)$_2$—, —(CH$_2$)$_3$—, —(CH$_2$)$_4$—, and —(CH$_2$)$_5$—; wherein $L^7$ is optionally present, and when present, $L^7$ is selected from —CH$_2$—, —(CH$_2$)$_2$—, —(CH$_2$)$_3$—, —(CH$_2$)$_4$—, and —(CH$_2$)$_5$—; wherein $L^8$ is optionally present, and when present, $L^8$ is selected from —CH$_2$—, —(CH$_2$)$_2$—, —(CH$_2$)$_3$—, —(CH$_2$)$_4$—, and —(CH$_2$)$_5$—; wherein each of $Q^5$ and $Q^6$ is independently selected from —CH— and N, provided that $Q^6$ and $L^6$ are not simultaneously N; wherein each of $A^3$ and $A^4$ is independently selected from —N— or —CH—; wherein each of $R^{31}$ and $R^{32}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; wherein each of $R^{35}$, $R^{36}$, $R^{37}$, $R^{38}$, and $R^{39}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; and wherein each of $R^{310}$, $R^{311}$, $R^{312}$, $R^{313}$, and $R^{314}$ is independently selected from hydrogen, halogen, cyano, hydroxyl, —NH$_2$, —SF$_5$, —O(C1-C6 alkyl), —S(C1-C6 alkyl), C1-C6 haloalkyl, and C1-C6 hydroxyalkyl; or a pharmaceutically acceptable salt thereof.

In an aspect, the disclosure pertains to compounds which bind a pocket in ANGPTL4 described by FIGS. 11A-12B. In an aspect, the compound binds the pocket in ANGPTL4 with a binding affinity of about ≤10 kcal/mol when determined using Vina Affinity software. In an aspect, the compound binds the pocket in ANGPTL4 with a binding affinity of about ≤10 kcal/mol when determined using SwissDock Affinity software.

Figure 12A:
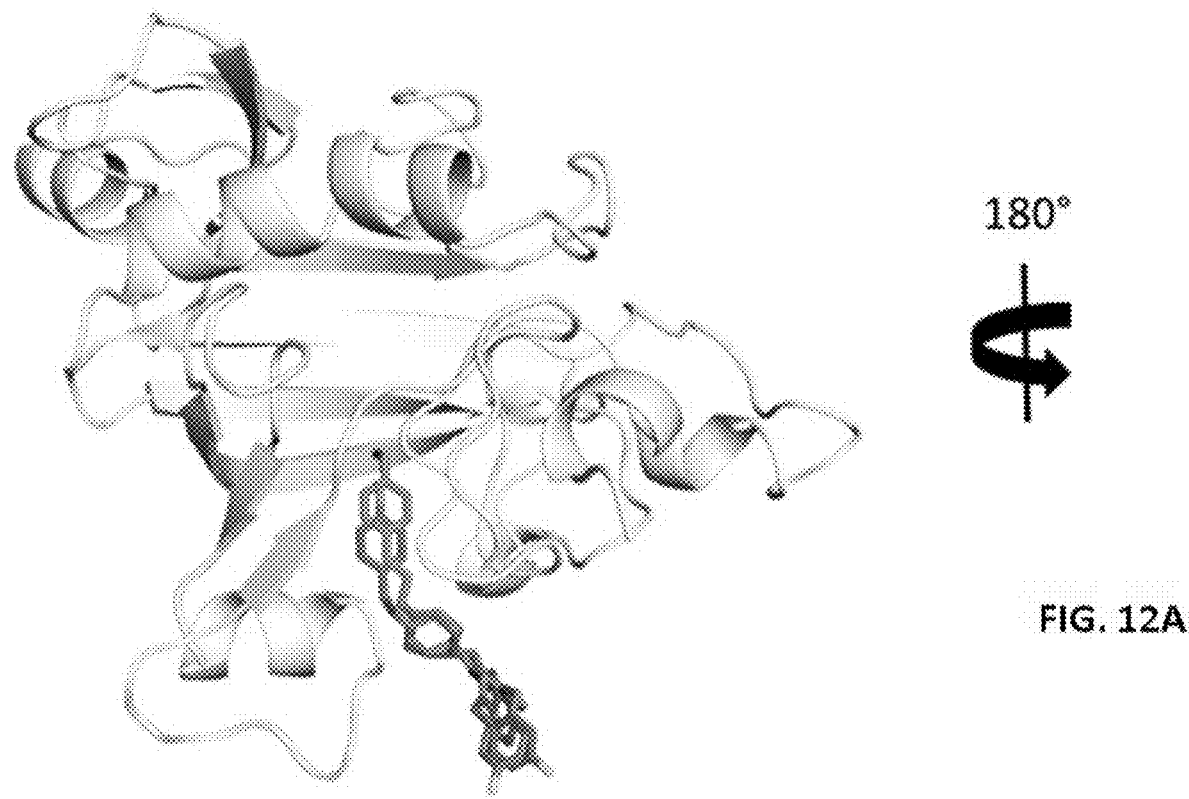
FIGS. 12A and 12B show a representative model for binding of astemizole within a pocket of ANGPTL4 within the C-terminal portion of the protein.
Figure 12B:
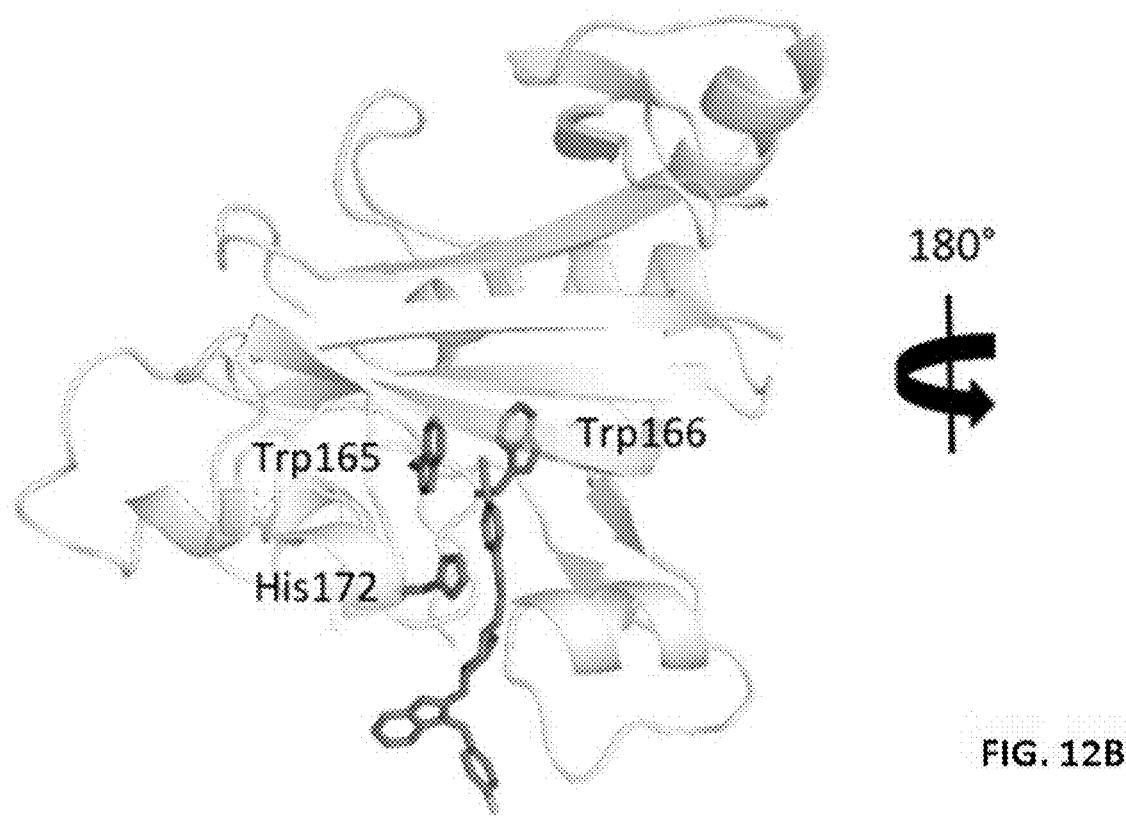

In an aspect, the disclosure pertains to compounds which bind a pocket of ANGPTL4 described by FIG. 12B, comprising interaction of the compound with at least one of Trp154, Trp166, or His172 in ANGPTL4. In an aspect, the disclosure pertains to compounds which bind a pocket of ANGPTL4 described by FIG. 12B, comprising interaction of the compound with at least one of Trp154, Trp166, or His172 in ANGPTL4, with an overall binding affinity of about ≤10 kcal/mol when determined using Vina Affinity software. In an aspect, the disclosure pertains to compounds which bind a pocket of ANGPTL4 described by FIG. 12B, comprising interaction of the compound with at least one of Trp154, Trp166, or His172 in ANGPTL4, with an overall binding affinity of about ≤10 kcal/mol when determined using SwissDock Affinity software.

In an aspect, the compound has a structure represented by a formula listed below:

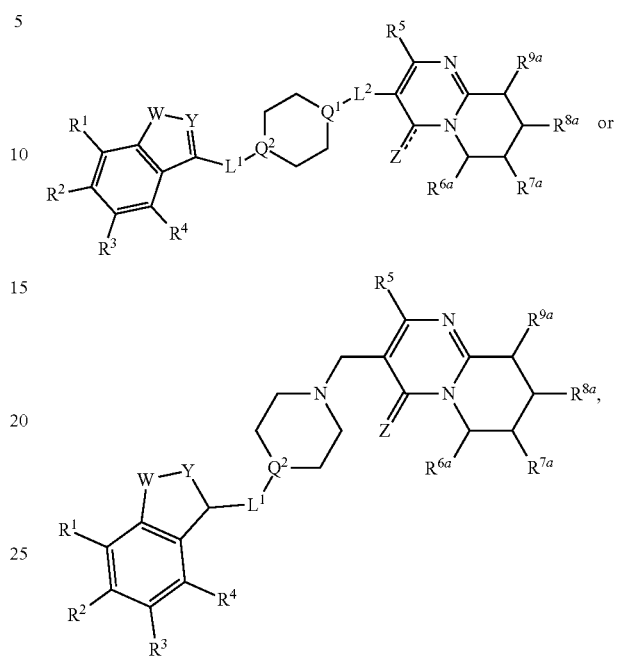

wherein all variables are as defined herein.

In an aspect, the compound has a structure represented by a formula listed below:

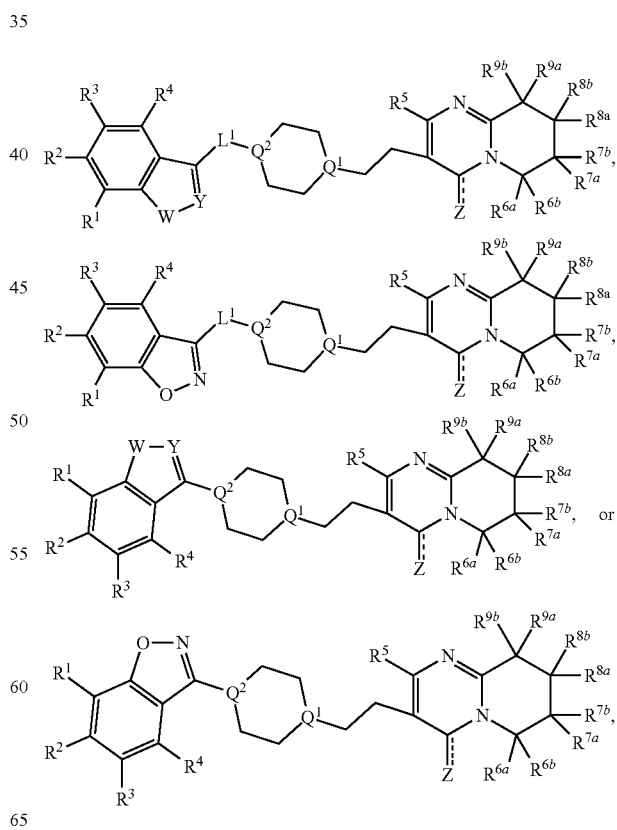

wherein all variables are as defined herein.

In an aspect, the compound has a structure represented by a formula listed below:

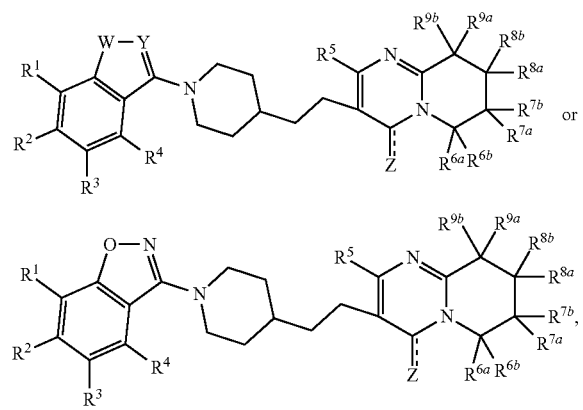

wherein all variables are as defined herein.

In an aspect, the compound has a structure represented by a formula listed below:

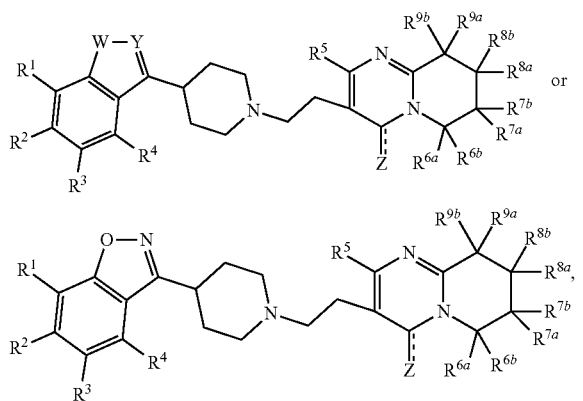

wherein all variables are as defined herein.

In an aspect, the compound has a structure represented by a formula listed below:

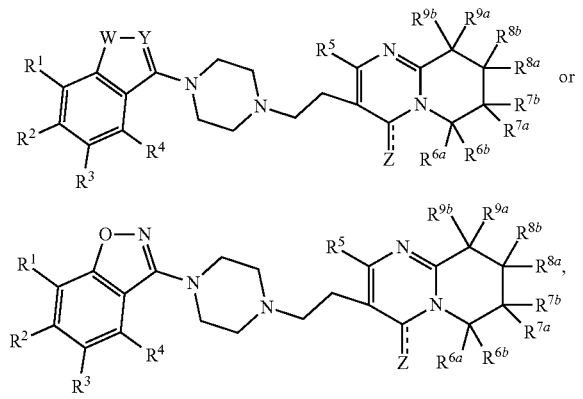

wherein all variables are as defined herein.

In an aspect, the compound has a structure represented by a formula listed below:

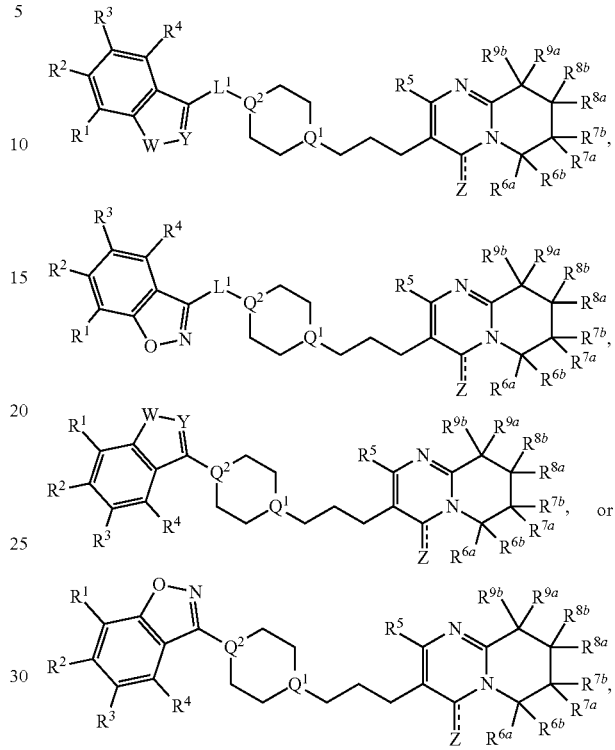

wherein all variables are as defined herein.

In an aspect, the compound has a structure represented by a formula listed below:

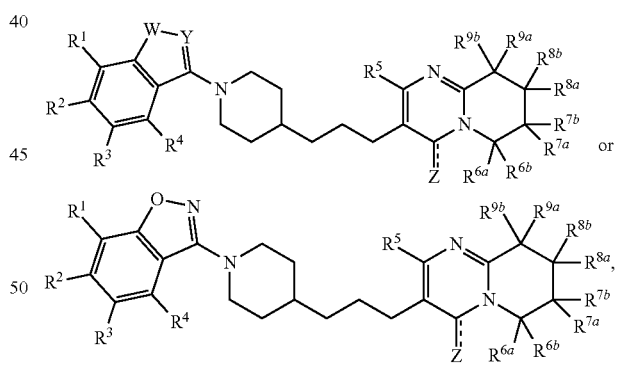

wherein all variables are as defined herein.

In an aspect, the compound has a structure represented by a formula listed below:

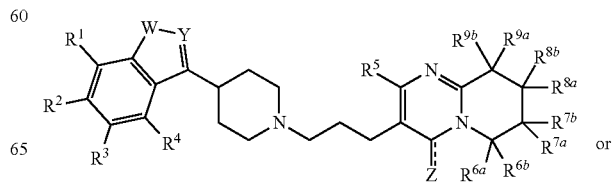

-continued

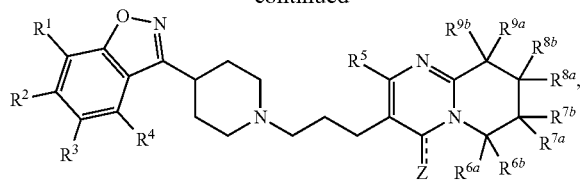

wherein all variables are as defined herein.

In an aspect, the compound has a structure represented by a formula listed below:

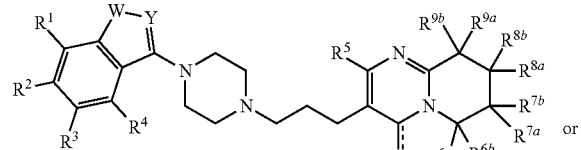

or

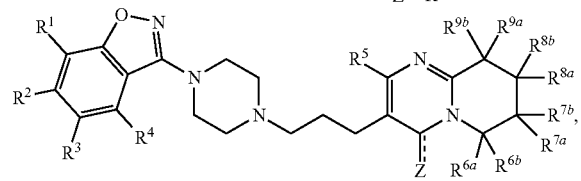

wherein all variables are as defined herein.

In an aspect, the compound has a structure represented by a formula listed below:

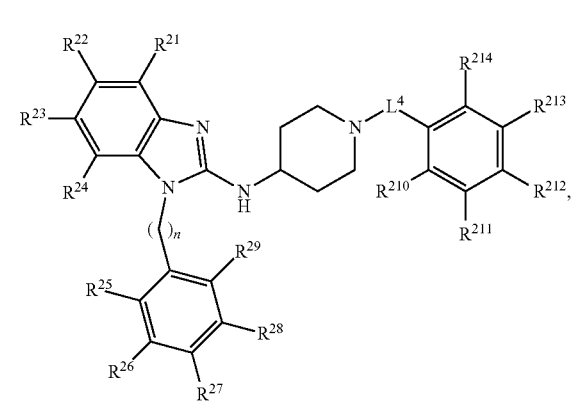

wherein n is an integer with a value of 1, 2, 3, 4, or 5; and wherein all variables are as defined herein.

In an aspect, the compound has a structure represented by a formula listed below:

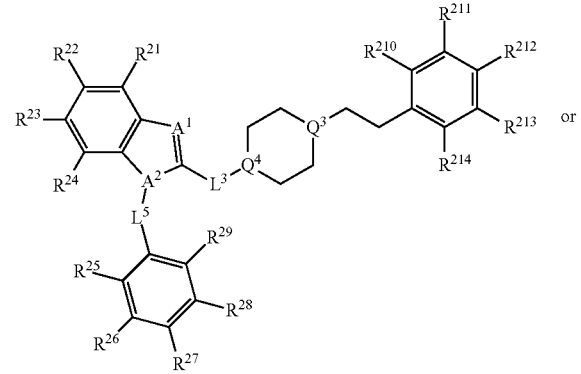

or

-continued

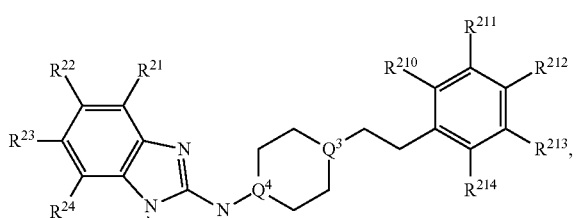

wherein all variables are as defined herein.

In an aspect, the compound has a structure represented by a formula listed below:

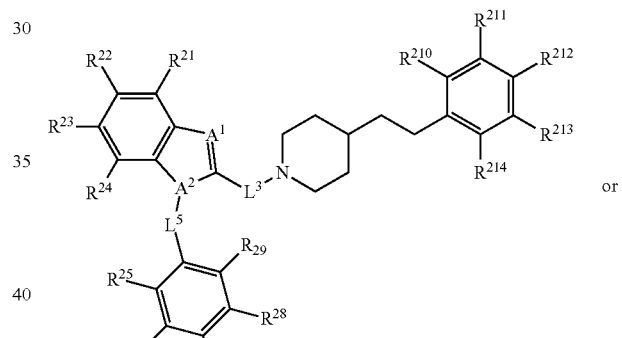

or

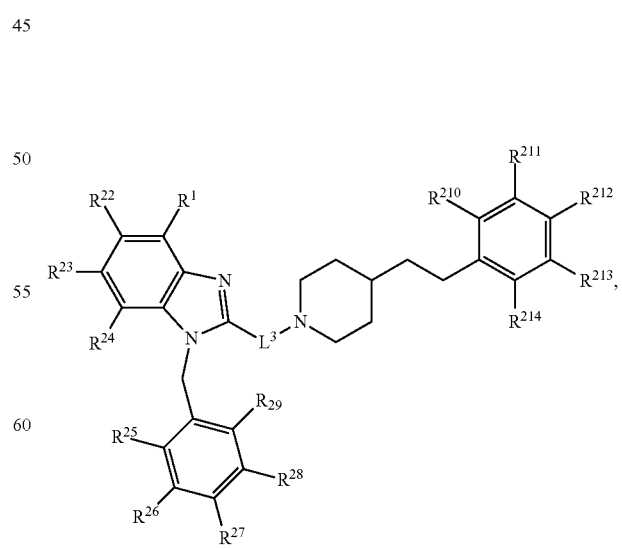

wherein all variables are as defined herein.

In an aspect, the compound has a structure represented by a formula listed below:

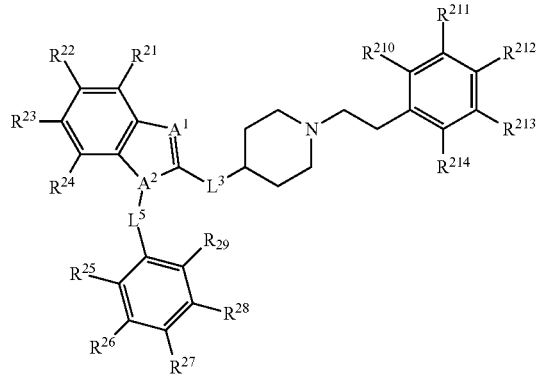

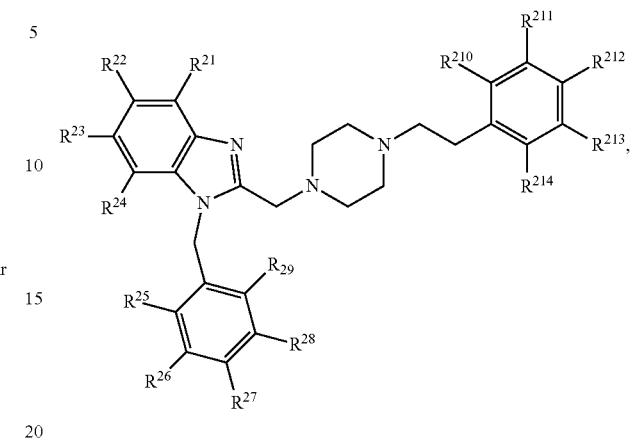

wherein all variables are as defined herein.

In an aspect, the compound has a structure represented by a formula listed below:

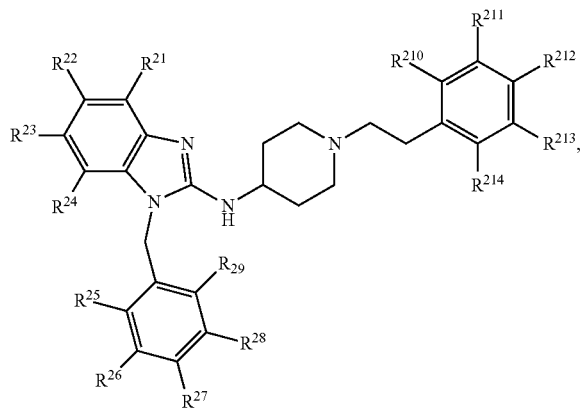

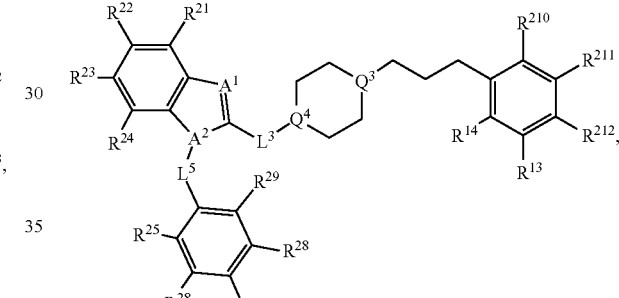

wherein all variables are as defined herein.

In an aspect, the compound has a structure represented by a formula listed below:

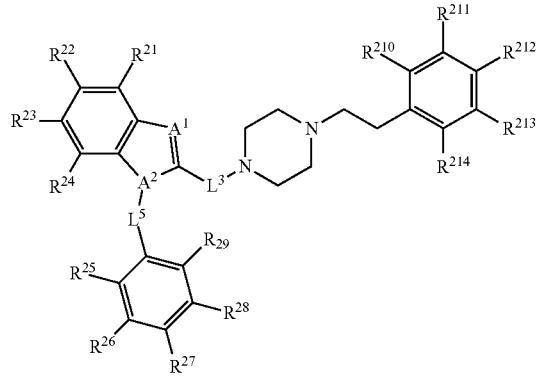

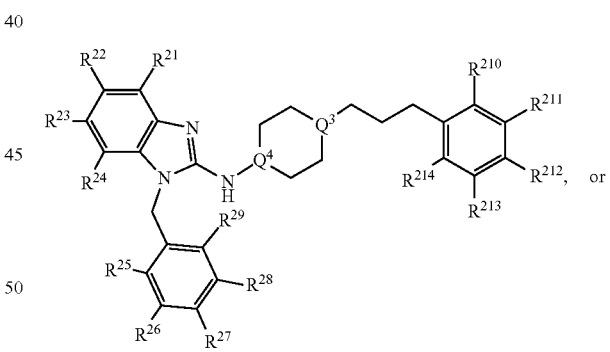

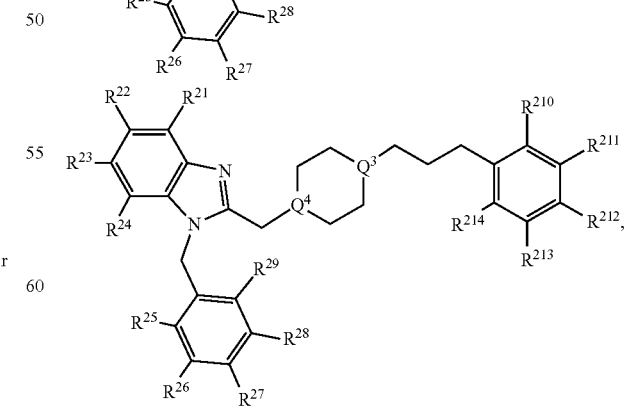

wherein all variables are as defined herein.

In an aspect, the compound has a structure represented by a formula listed below:
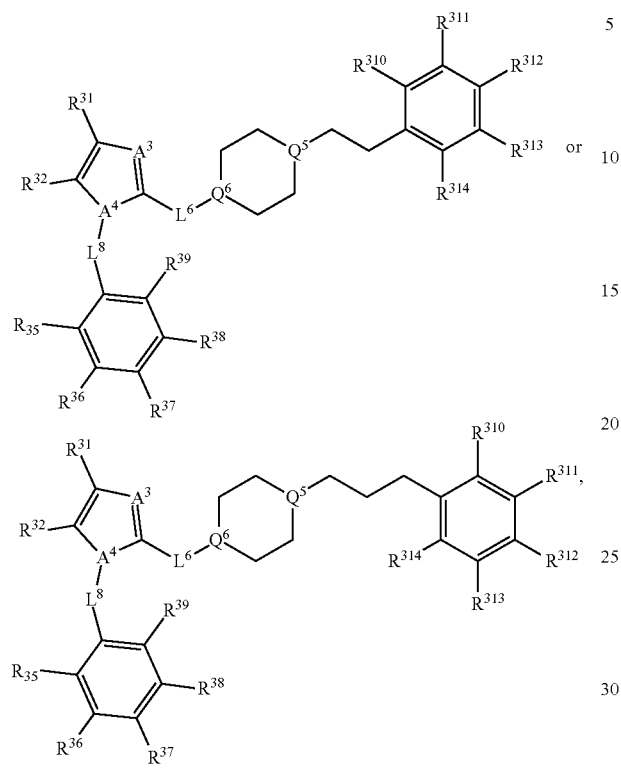
wherein all variables are as defined herein.
In an aspect, a compound can be present as one or more of the following structures:
-continued
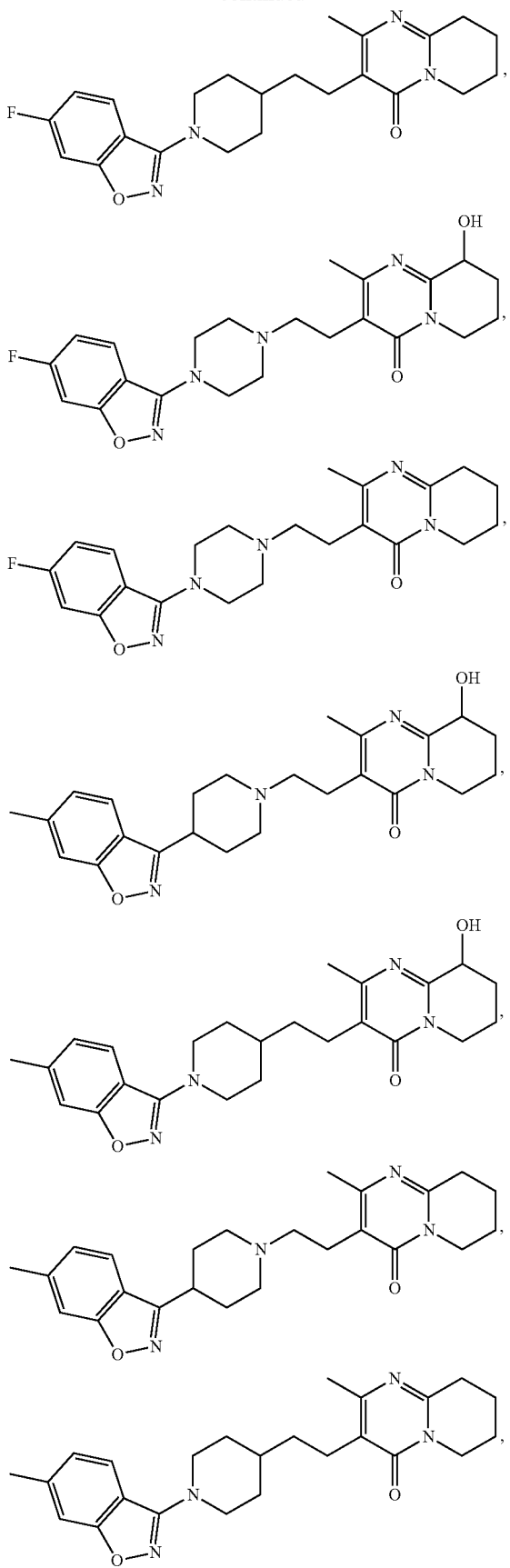

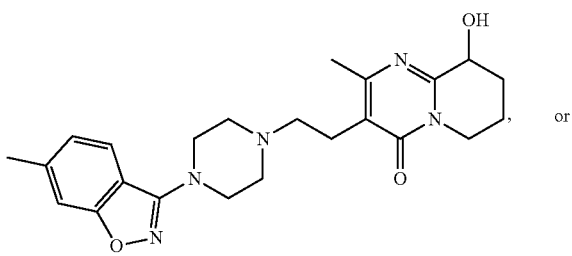
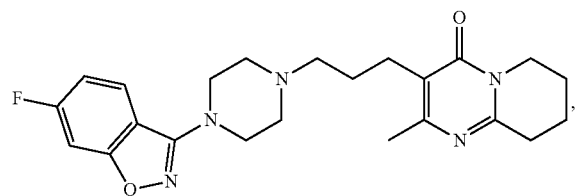
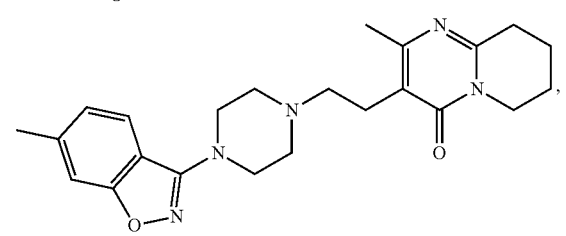
or subgroups thereof.
In an aspect, a compound can be present as one or more of the following structures:
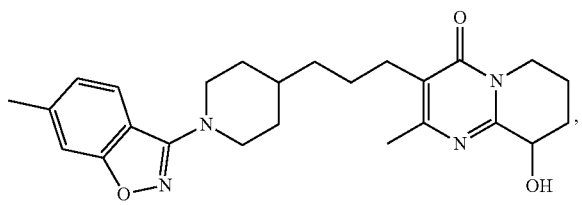
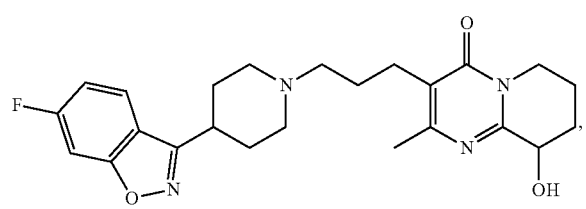
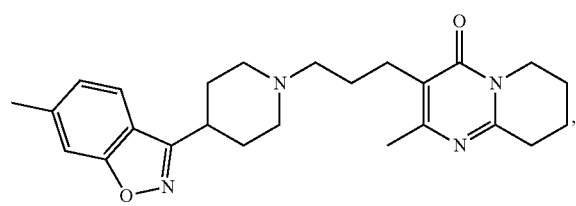
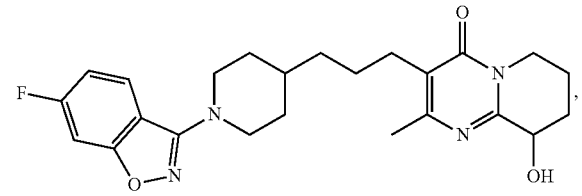
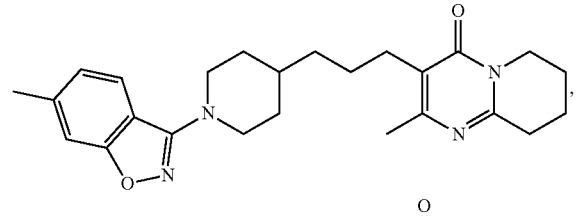
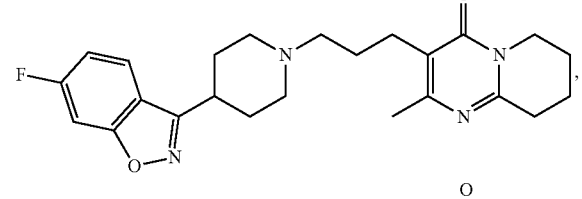
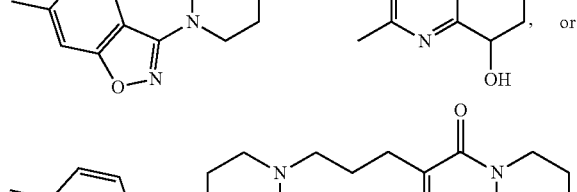
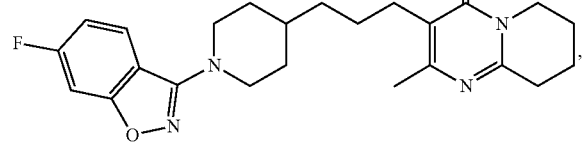
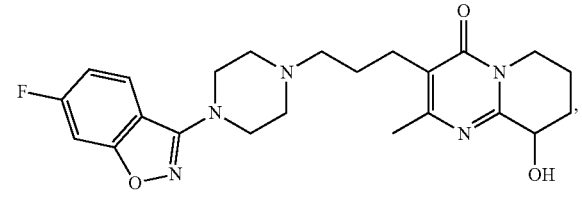
or subgroups thereof.

In an aspect, a compound can be present as one or more of the following structures:
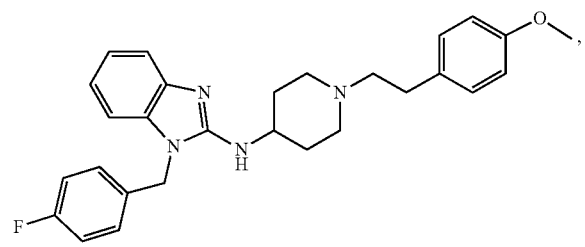
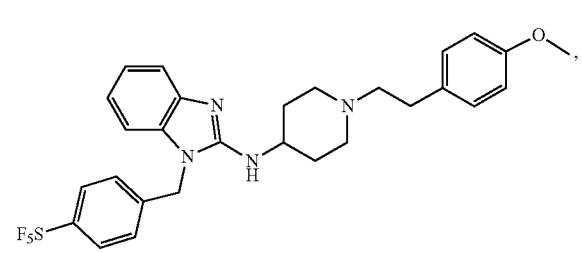
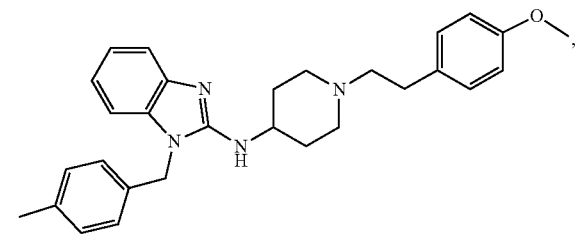
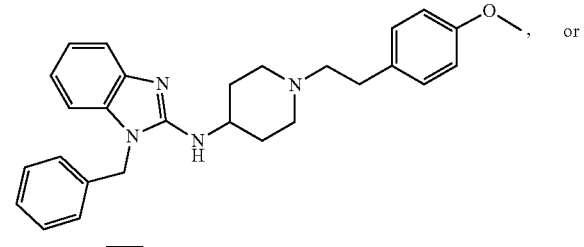
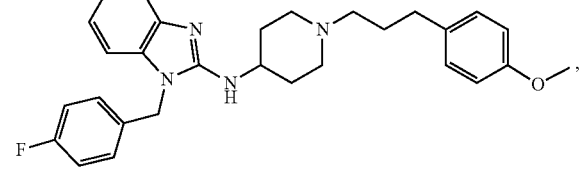
or subgroups thereof.
In an aspect, a compound can be present as one or more of the following structures:
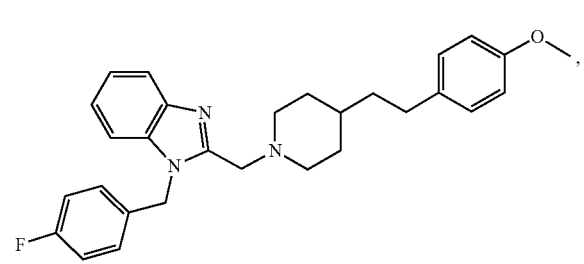
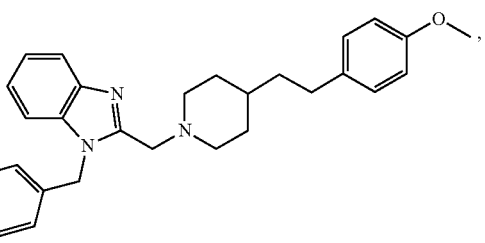
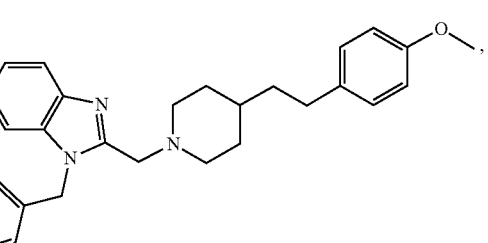
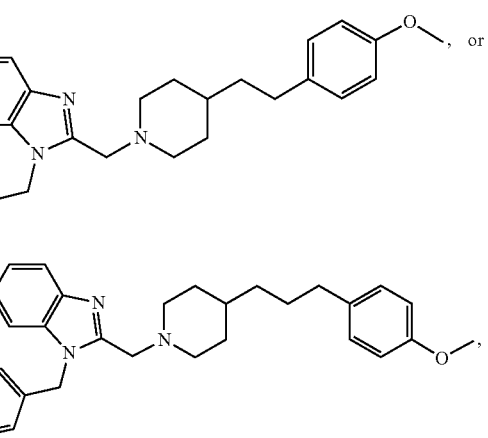
or subgroups thereof.
In an aspect, a compound can be present as one or more of the following structures:
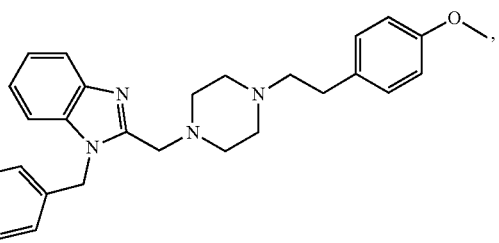
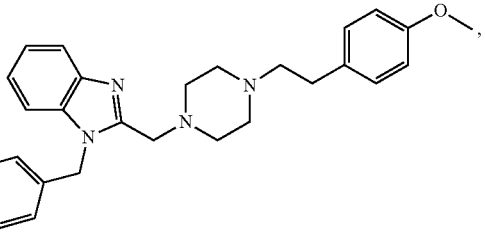

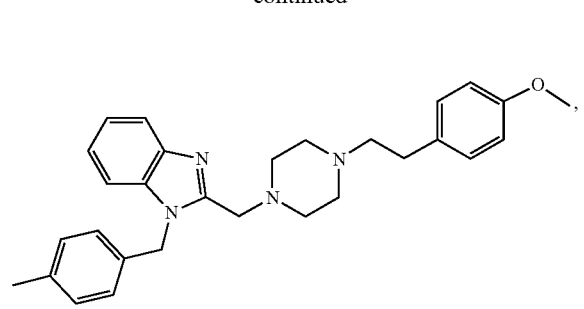
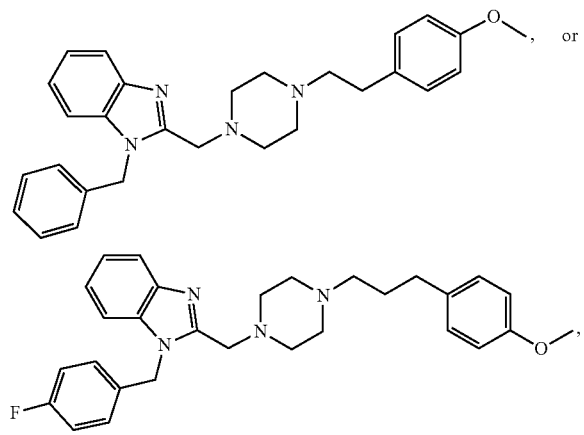
or subgroups thereof.
In an aspect, a compound can be present as one or more of the following structures:
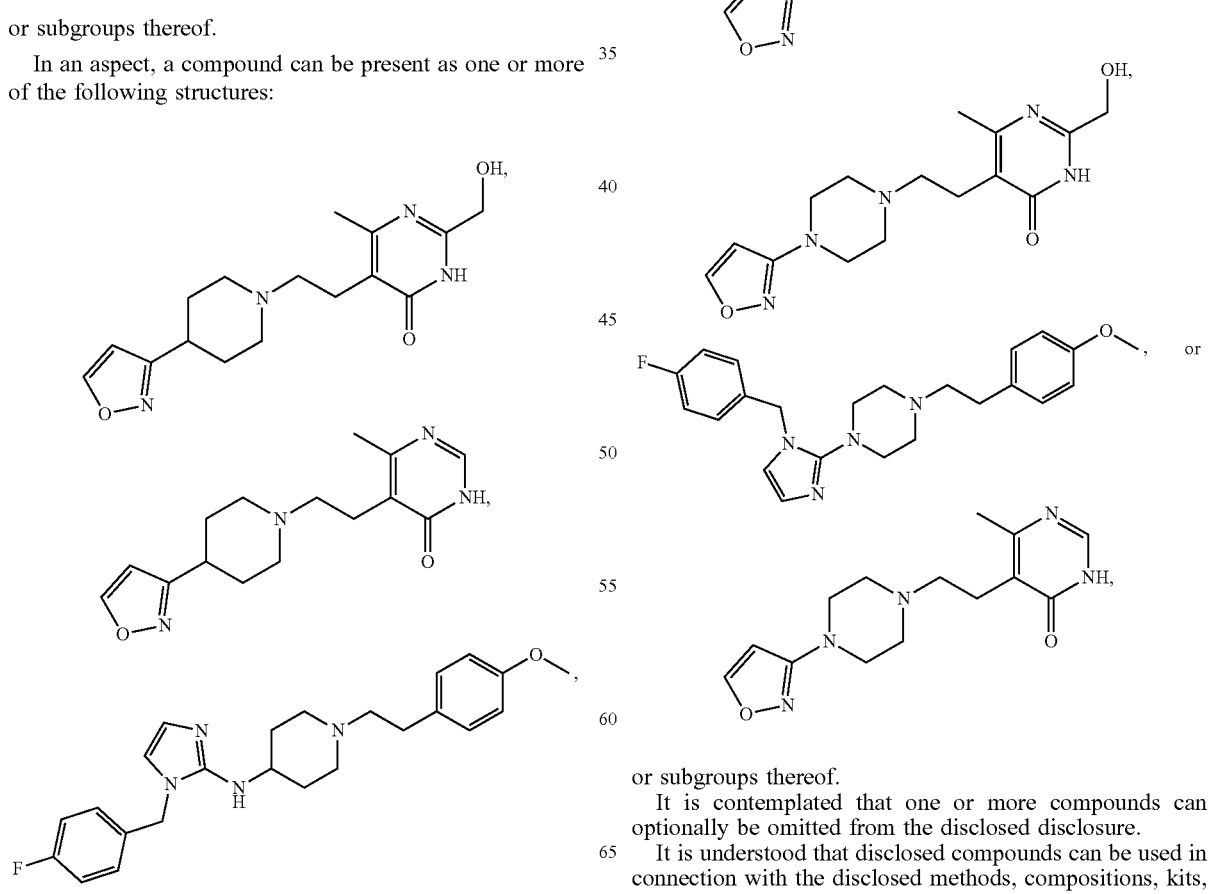
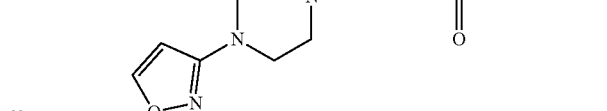
or subgroups thereof.
It is contemplated that one or more compounds can optionally be omitted from the disclosed disclosure.
It is understood that disclosed compounds can be used in connection with the disclosed methods, compositions, kits, and uses.

It is understood that pharmaceutical acceptable derivatives of disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

In an aspect, the disclosure pertains to methods of making compounds useful as inhibitors of ANGPTL4, which can be useful in the treatment of disorders of uncontrolled cellular proliferation associated with an ANGPTL4 dysfunction and other diseases in which ANGPTL4 is involved. In an aspect, the disclosure pertains to the disclosed synthetic manipulations. In an aspect, the disclosed compounds comprise the products of the synthetic methods described herein. In an aspect, the disclosed compounds comprise a compound produced by a synthetic method described herein. In an aspect, the disclosure comprises a pharmaceutical composition comprising a therapeutically effective amount of the product of the disclosed methods and a pharmaceutically acceptable carrier. In an aspect, the disclosure comprises a method for manufacturing a medicament comprising combining at least one compound of any of disclosed compounds or at least one product of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

In an aspect, disclosed modulators of ANGPTL4 can be prepared generically by the synthetic scheme as shown below.

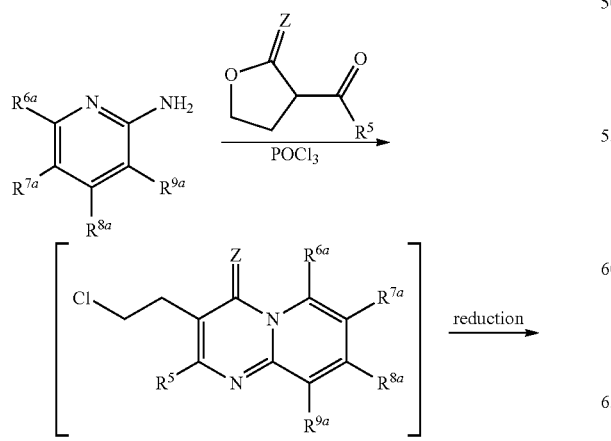

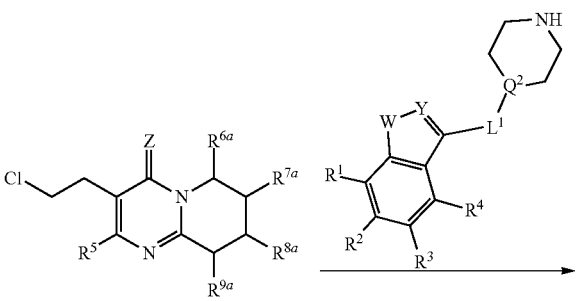

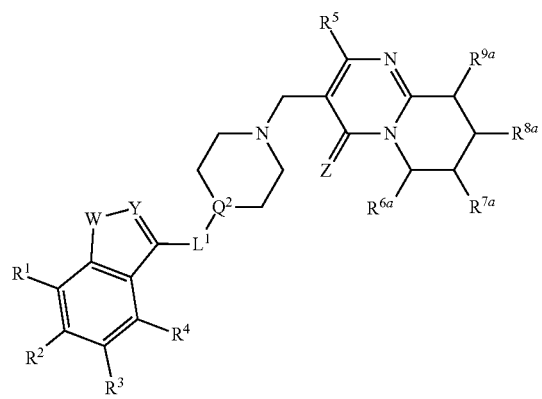

Compounds are represented in generic form, with substituents as noted in compound descriptions elsewhere herein. A more specific example is set forth below.

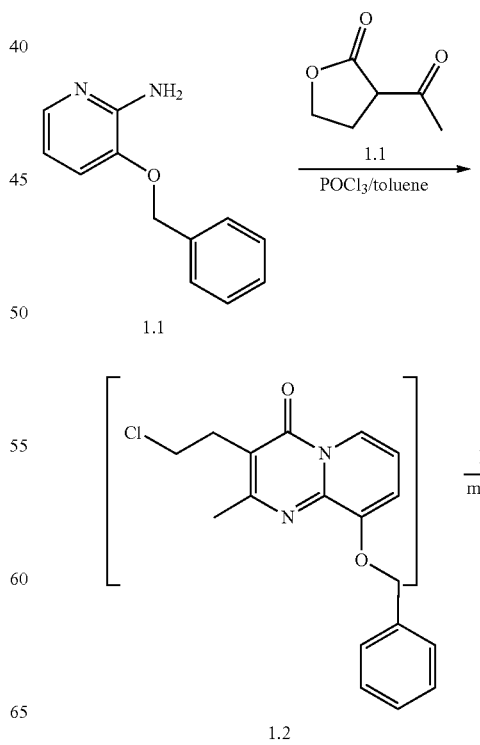

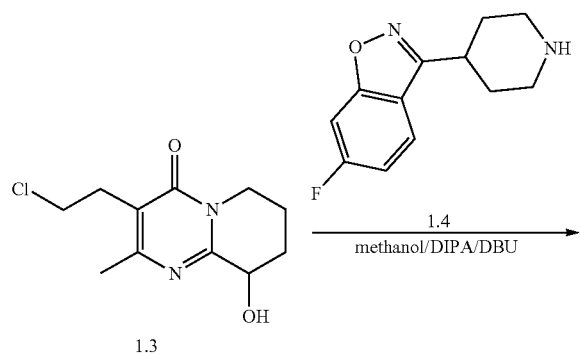

described in the literature. The reaction is carried out in the present of catalytic amounts of DBU in the presence of about a 2:1 molar ratio of DIPA to compound 1.3 in a suitable solvent, e.g., methanol. The reaction is carried out at a suitable temperature, e.g., about 50° C. to about 65° C., over a suitable period of time, e.g., about 24 hours to about 45 hours. Completeness of the reaction can be monitored by a suitable method such as TLC or HPLC. The desired product can be isolated by precipitation, and further purified by suitable methods precipitation, filtration, and/or column chromatography.

In an aspect, disclosed modulators of ANGPTL4 can be prepared generically by the synthetic scheme as shown below.

In an aspect, compounds of the present disclosure, e.g. compounds of Formula 1.3 can be prepared beginning with reaction of compounds of Formulas 1.1 and 1.2 to yield compounds of Formula 1.3. Compounds of Formula 1.1, i.e. substituted pyridine analogs, can be obtained from commercial sources or can be readily prepared by skilled in the art according to methods described in the literature. Compound 1.1 and related analogues, i.e., 3-alkyldihyrofuranones, are available commercially. The reaction of the substituted pyridine analog with the 3-alkyldihyrofuranone is typically carried out in a suitable solvent, e.g., toluene, at a suitable temperature, e.g., about 25° C. to about 30° C., for a suitable period of time, e.g. about 30 minutes to about 90 minutes, followed by addition of phosphorus oxychloride at a suitable temperature, e.g., about 45° C. to about 60° C., over a suitable period of time, e.g., about 2 hours to about 5 hours, followed by further reaction at a suitable temperature, e.g., about 60° C. to about 75° C., over a suitable period of time, e.g., about 20 hours to about 42 hours. The unreacted phosphoryl oxychloride and toluene are removed under reduced pressure distillation (below about 75° C.), followed by extraction with toluene and water. The isolated material is then subjected to reductive hydrogenation using a suitable catalyst, e.g., palladium, at a suitable temperature, e.g., about 45° C. to about 60° C., over a suitable period of time, e.g., about 16 hours to about 30 hours. The product, compound 1.3, is isolated extraction with a suitable solvent, e.g., chloroform, and precipitation.

The final desired product, compound 1.5, can be obtained by reaction of compound 1.3, prepared as described in the preceding step, with a suitable substituted piperidine (as shown in compound 1.4) or piperazine analog. Compounds of Formula 1.4, i.e. substituted piperidine or piperazine analogs, can be obtained from commercial sources or can be readily prepared by skilled in the art according to methods

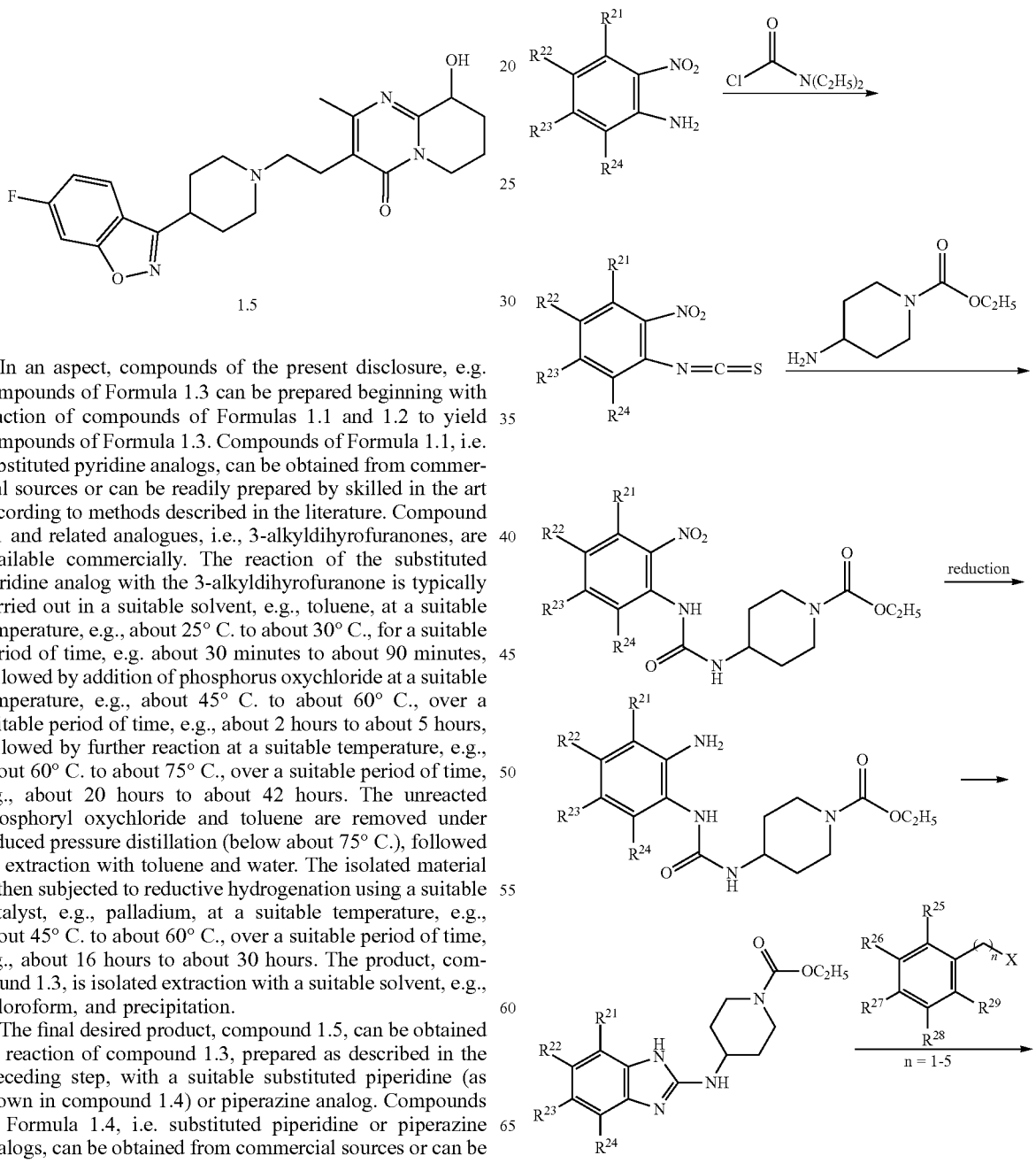

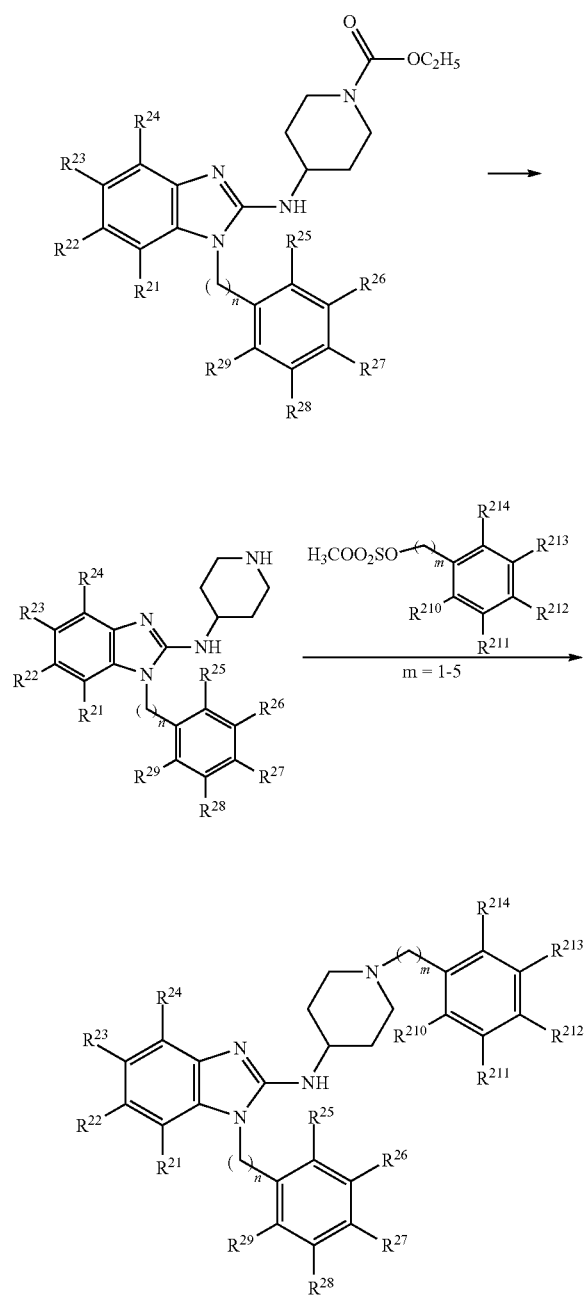
Compounds are represented in generic form, with substituents as noted in compound descriptions elsewhere herein. A more specific example is set forth below.
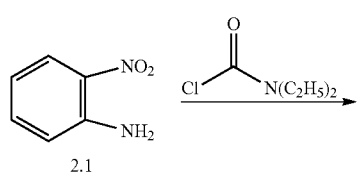
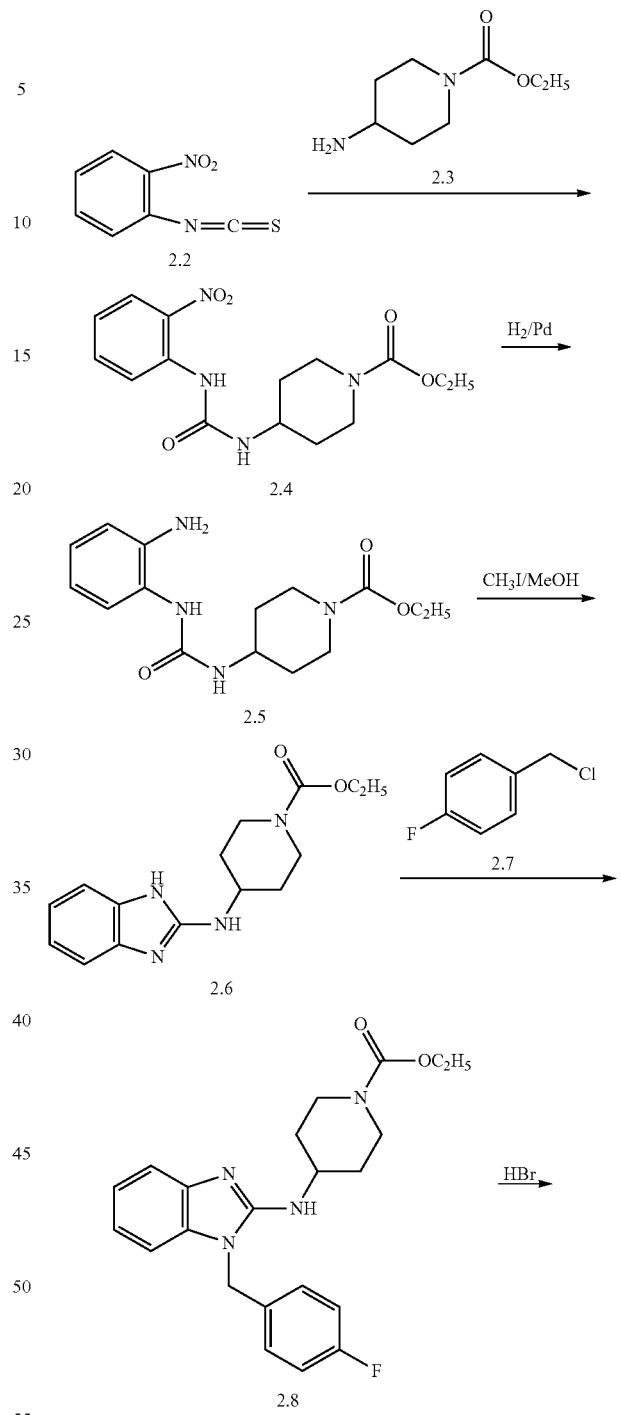
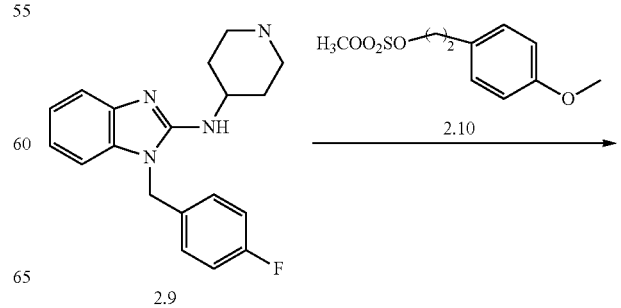

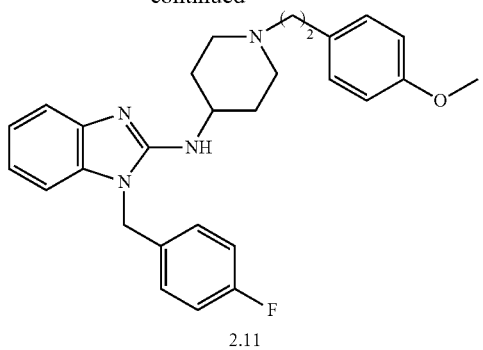

2.11

In an aspect, compounds of the present disclosure, e.g., compounds of Formula 2.1, can be prepared in a multi-step synthesis beginning with reaction of compound of Formulas 2.1, a 2-nitroaniline, or an appropriately substituted analogue thereof, and diethylcarbamic chloride top yield the desired 1-isothiocyanato-2-nitrobenzene, a compound of Formula 2.2, or an appropriately substituted analogue thereof. Suitable compounds of Formula 2.1, i.e., substituted 2-nitroaniline analogs, can be obtained from commercial sources or can be readily prepared by skilled in the art according to methods described in the literature. Compounds of Formula 2.4 can be prepared using the appropriately substituted 1-isothiocyanato-2-nitrobenzene analog, such as Compound 2.2, in reaction with an appropriately substituted ethyl 4-aminopiperidine-1-carboxylate analog, such as Compound 2.3, with a suitable protecting group on the amino group located within the ring of the piperidine moiety, e.g., an ethyl carboxylate group. The resulting product is subjected to reductive hydrogen, e.g., reaction in the presence of hydrogen gas and a catalyst, such as palladium, to yield Compound 2.5. Cyclization to form the benzoimidazole moiety is carried out in the presence of methyl iodide and a solvent such as methanol. The amino group of the benzoimidazole can be alkylated using a suitable substituted chloromethyl compound, such as Compound 2.7, followed by removal of the ester protecting group in the presence of a suitable acid, e.g., HBr, to yield the desired product such as Compound 2.9. Suitable substituted chloromethyl compounds are available commercially or can be prepared by standard methods known to one skilled in the art. The final step involves reaction of the prepared benzoimidazolyl piperidinyl analogue, e.g., Compound 2.9, with an appropriate methyl sulfate compound, such as Compound 2.10, to yield the desired modulator of ANGPTL4, e.g., Compound 2.11.

Several methods for preparing the compounds of this disclosure are illustrated in the preceding general examples. Starting materials and the requisite intermediates are in some cases commercially available, or can be prepared according to literature procedures or as illustrated herein. The preceding examples are provided herein to illustrate the disclosure, and should not be construed as limiting the disclosure in any way. The examples are typically depicted in free base form, according to the IUPAC naming convention. Examples are provided herein to illustrate the disclosure, and should not be construed as limiting the disclosure in any way.

The disclosed methods of making can provide compounds that can contain one or more asymmetric centers and, thus, potentially give rise to enantiomers and diastereomers. Unless stated to the contrary, the compounds prepared by the disclosed methods include all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included.

In an aspect, the disclosed methods of making can provide racemic mixtures that can be resolved to pure or substantially pure enantiomers using chiral phase chromatography or other suitable methods known to one skilled in the art. As known to one skilled in the art, a variety specific columns and/or mobile phases can affect the desired resolution of enantiomers, and the specific choice can be determined by one skilled in the art. As known to one skilled in the art, chiral chromatography can be carried out in a variety of formats (e.g. SFC, HPLC, and SMB), and other formats can be used to obtain similar results. Moreover, other suitable methods known to one skilled in the art for the separation and isolation of individual enantiomers from a racemic or scalemic mixture can be used to isolate specific enantiomers as needed, e.g., fractional crystallization or coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

In an aspect, the disclosure pertains to pharmaceutical compositions comprising disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In an aspect, the disclosure pertains to pharmaceutical compositions comprising a pharmaceutically acceptable carrier and an effective amount of at least one disclosed compound; or a pharmaceutically acceptable salt thereof.

In an aspect, the effective amount is a therapeutically effective amount. In an aspect, the effective amount is a prophylactically effective amount. In an aspect, the pharmaceutical composition comprises a compound that is a product of a disclosed method of making.

In an aspect, the pharmaceutical composition comprises a disclosed compound. In an aspect, the pharmaceutical composition comprises a product of a disclosed method of making.

In an aspect, the pharmaceutical composition comprises a therapeutically effective amount of a compound having a structure represented by a formula:

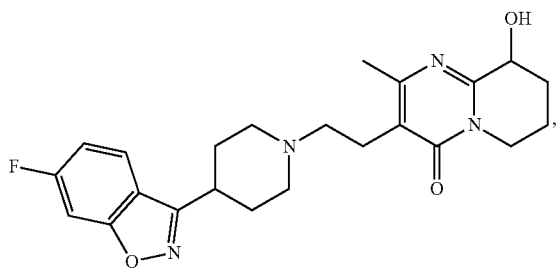

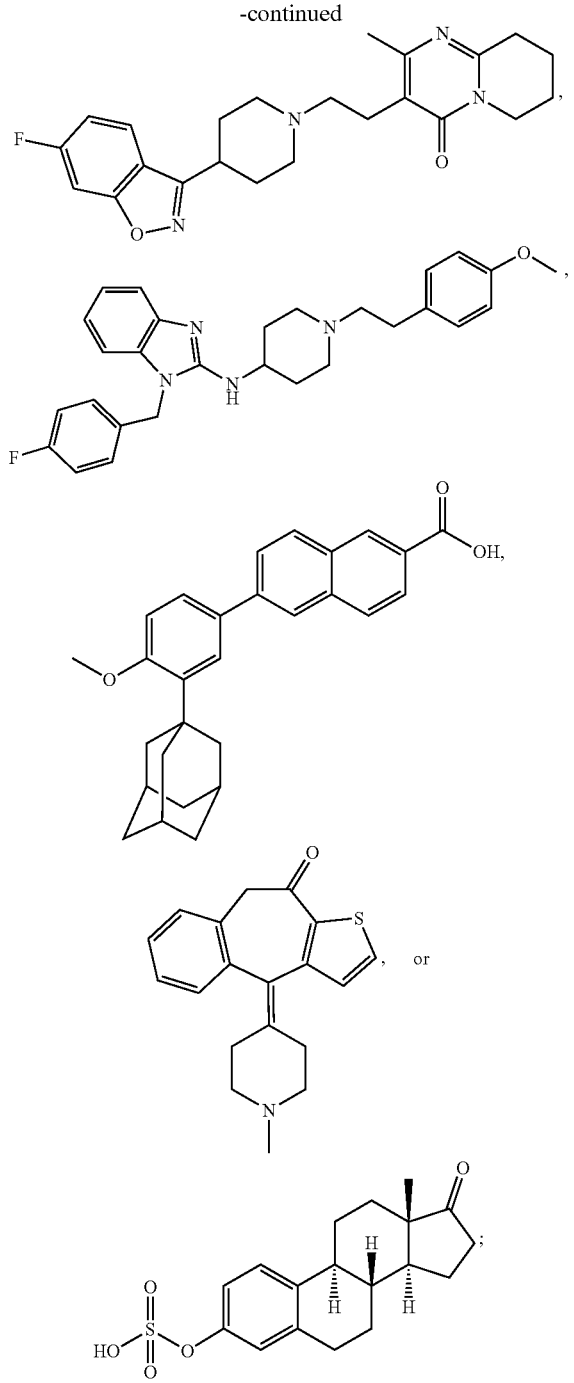

or a pharmaceutically acceptable salt thereof, and a pharmaceutically acceptable carrier.

In an aspect, the pharmaceutical composition exhibits modulation of ANGPTL4 activity with an $IC_{50}$ of less than about 50 μM, 25 μM, 10 μM, 5 μM, 1 μM, 500 nM, 250 nM, 100 nM, 50 nM, 25 nM, 10 nM, 5 nM, or 1 nM. In an aspect, modulation of ANGPTL4 activity is inhibition of ANGPTL4 activity.

In an aspect, the pharmaceutical composition exhibits inhibition of cellular proliferation with an $IC_{50}$ of less than about 50 μM, 25 μM, 10 μM, 5 μM, 1 μM, 500 nM, 250 nM, 100 nM, 50 nM, 25 nM, 10 nM, 5 nM, or 1 nM.

In an aspect, the pharmaceutical composition is used to treat a mammal. In an aspect, the mammal is a human. In an aspect, the mammal has been diagnosed with a need for treatment of the disorder prior to the administering step. In an aspect, the mammal has been identified to be in need of treatment of the disorder. In an aspect, the pharmaceutical composition is used to treat a disorder of uncontrolled cellular proliferation. In an aspect, the disorder is associated with an ANGPTL4 dysfunction.

In an aspect, the pharmaceutical composition is used to treat a cancer. In an aspect, the pharmaceutical composition is used to treat a cancer such as a pancreatic cancer, breast cancer, renal cancer, gastric cancer, colorectal cancer, lymphoma, cancers of the brain, genitourinary tract cancer, lymphatic system cancer, stomach cancer, larynx cancer, lung cancer, and malignant melanoma. In an aspect, the pharmaceutical composition is used to treat a pancreatic cancer.

In an aspect, the pharmaceutical composition is used to treat a gemcitabine-resistant cancer. In an aspect, the pharmaceutical composition is used to treat a gemcitabine-resistant cancer such as a gemcitabine-resistant pancreatic cancer, gemcitabine-resistant breast cancer, gemcitabine-resistant renal cancer, gemcitabine-resistant gastric cancer, gemcitabine-resistant colorectal cancer, gemcitabine-resistant lymphoma, gemcitabine-resistant cancers of the brain, gemcitabine-resistant genitourinary tract cancer, gemcitabine-resistant lymphatic system cancer, gemcitabine-resistant stomach cancer, gemcitabine-resistant larynx cancer, gemcitabine-resistant lung cancer, and gemcitabine-resistant melanoma. In an aspect, the pharmaceutical composition is used to treat a gemcitabine-resistant pancreatic cancer.

In certain aspects, the disclosed pharmaceutical compositions comprise disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present disclosure is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the disclosure, or pharmaceutically acceptable salts thereof, of this disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this disclosure can include a pharmaceutically acceptable carrier and a compound or a pharmaceutically acceptable salt of the compounds of the disclosure. The compounds of the disclosure, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this disclosure can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present disclosure comprise a compound of the disclosure (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present disclosure suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present disclosure can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the disclosure, and/or pharmaceutically acceptable salts thereof, can also be prepared in powder or liquid concentrate form.

In the treatment conditions which require modulation of ANGPTL4 activity, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present disclosure is further directed to a method for the manufacture of a medicament for modulating ANGPTL4 activity (e.g., treatment of one or more disorder of uncontrolled cellular proliferation associated with ANGPTL4 dysfunction) in mammals (e.g., humans) comprising combining one or more disclosed compounds, products, or compositions with a pharmaceutically acceptable carrier or diluent. Thus, in an aspect, the disclosure pertains to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed pharmaceutical compositions can be prepared from disclosed compounds. It is also understood that the disclosed pharmaceutical compositions can be employed in the disclosed methods of using.

The compounds disclosed herein are useful for treating, preventing, ameliorating, controlling or reducing the risk of a variety of disorders associated with uncontrolled cellular proliferation. For example, a treatment can include modulation of ANGPTL4 to an extent effective to a cancer. Thus, a disorder can be associated with ANGPTL4 activity. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

In an aspect, the disclosure pertains to a method for the treatment of a disorder of uncontrolled cellular proliferation, e.g., a cancer, in a mammal comprising the step of administering to the mammal at least one disclosed compound, or a pharmaceutically acceptable salt thereof, a disclosed pharmaceutical composition, or a disclosed medicament.

In an aspect, the disclosure pertains to a method for the treatment of a disorder of uncontrolled cellular proliferation in a mammal comprising the step of administering to the mammal an effective amount of at least one compound having a structure represented by a formula:

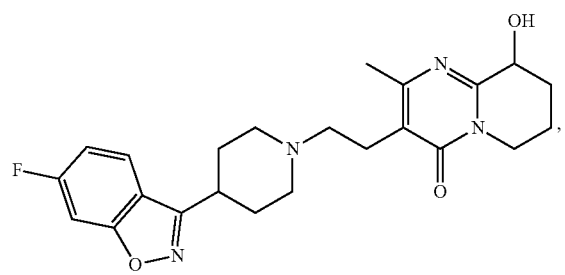

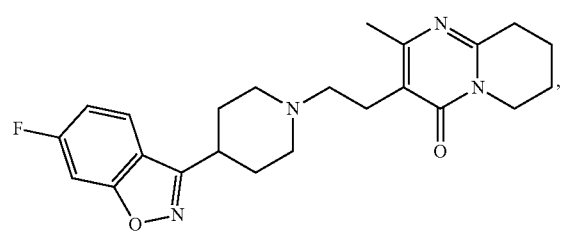

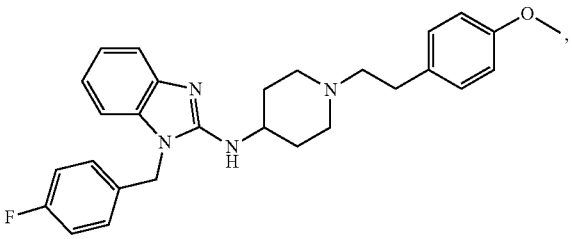

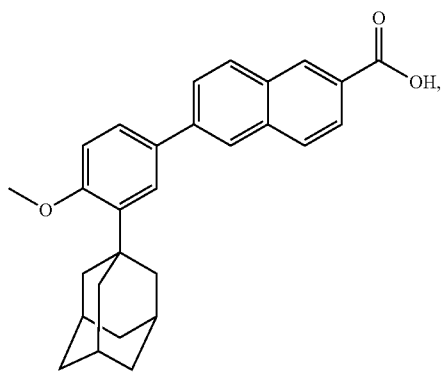

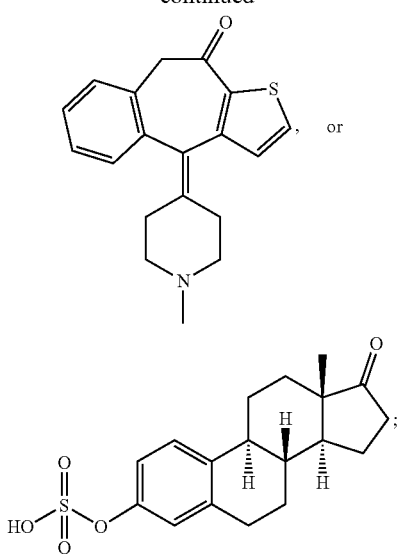

or a pharmaceutically acceptable salt thereof.

In an aspect, the disclosure pertains to a method for the treatment of a gemcitabine-resistant cancer, in a mammal comprising the step of administering to the mammal at least one disclosed compound, or a pharmaceutically acceptable salt thereof, a disclosed pharmaceutical composition, or a disclosed medicament.

In an aspect, the disclosure pertains to a method for the treatment of a gemcitabine-resistant cancer in a mammal comprising the step of administering to the mammal an effective amount of at least one compound having a structure represented by a formula:

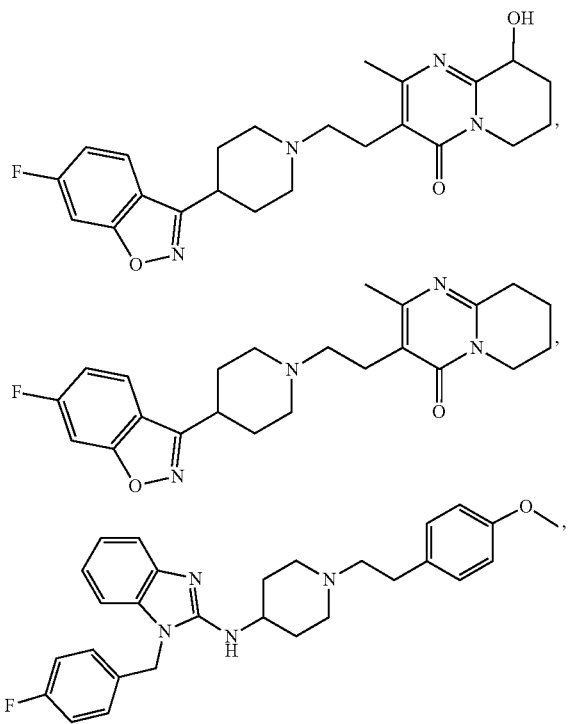

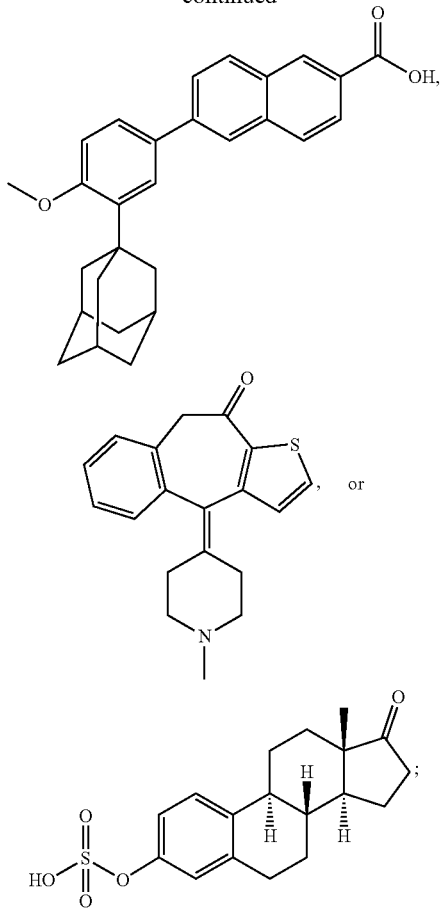

or a pharmaceutically acceptable salt thereof.

Also provided is a method for the treatment of one or more disorders, e.g., a cancer, associated with ANGPTL4 activity in a subject comprising the step of administering to the subject at least one disclosed compound; at least one disclosed pharmaceutical composition; or a disclosed medicament in a dosage and amount effective to treat the disorder in the subject.

In an aspect, the disclosure pertains to a method for modulation of ANGPTL4 activity in a mammal comprising the step of administering to the mammal an effective amount of at least one disclosed compound or a pharmaceutically acceptable salt thereof.

In an aspect, the disclosure pertains to a method for modulation of ANGPTL4 activity in a mammal comprising the step of administering to the mammal an effective amount of at least one compound having a structure represented by a formula:

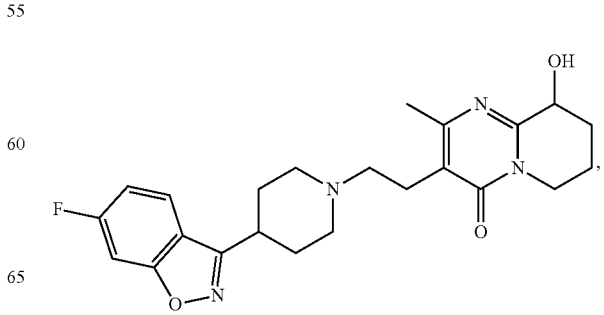

-continued

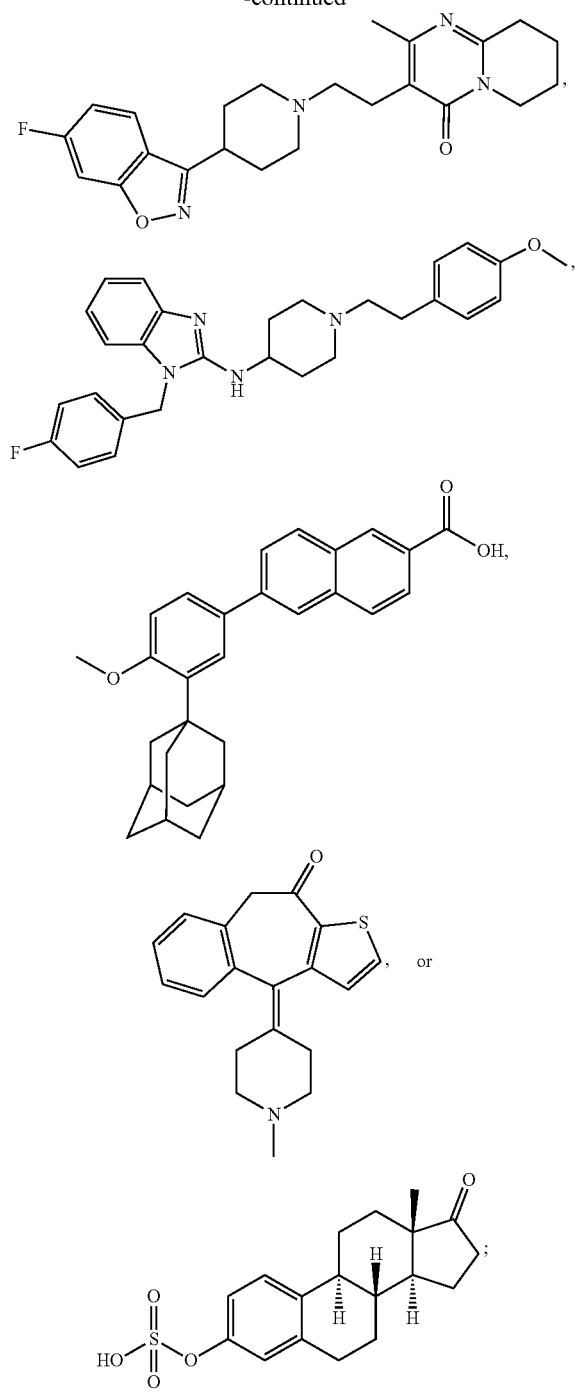

or a pharmaceutically acceptable salt thereof.

In an aspect, the disclosure pertains to a method for modulation of ANGPTL4 activity in at least one cell, comprising the step of contacting the at least one cell with an effective amount of at least one disclosed compound, or pharmaceutically acceptable salt thereof; at least one disclosed pharmaceutical composition; or a disclosed medicament in a dosage and amount effective to inhibit ANGPTL4 activity in the at least one cell.

In an aspect, the disclosure pertains to a method for modulation of ANGPTL4 activity in at least one cell, comprising the step of contacting the at least one cell with an effective amount of at least one compound having a structure represented by a formula:

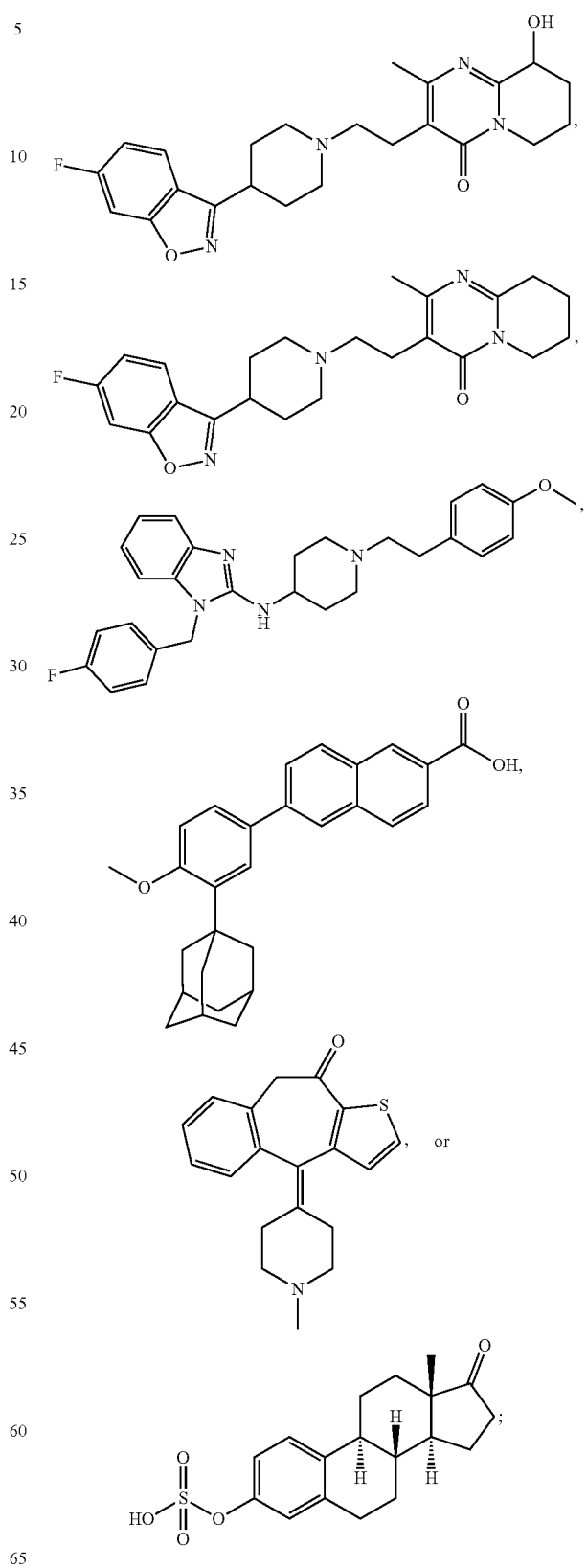

or a pharmaceutically acceptable salt thereof.

In an aspect, disclosed compounds have utility in treating a variety of cancers, e.g., a cancer associated with ANGPTL4 activity, including one or more of the following conditions or diseases: a pancreatic cancer, breast cancer, renal cancer, gastric cancer, colorectal cancer, lymphoma, cancers of the brain, genitourinary tract cancer, lymphatic system cancer, stomach cancer, larynx cancer, lung, pancreatic cancer, and malignant melanoma. In an aspect, disclosed compounds have utility in treating a pancreatic cancer.

In an aspect, disclosed compounds have utility in treating a variety of gemcitabine-resistant cancers, e.g., a cancer associated with ANGPTL4 activity, including one or more of the following gemcitabine-resistant cancers: gemcitabine-resistant pancreatic cancer, gemcitabine-resistant breast cancer, gemcitabine-resistant renal cancer, gemcitabine-resistant gastric cancer, gemcitabine-resistant colorectal cancer, gemcitabine-resistant lymphoma, gemcitabine-resistant cancers of the brain, gemcitabine-resistant genitourinary tract cancer, gemcitabine-resistant lymphatic system cancer, gemcitabine-resistant stomach cancer, gemcitabine-resistant larynx cancer, gemcitabine-resistant lung cancer, and gemcitabine-resistant melanoma. In an aspect, disclosed compounds have utility in treating a pancreatic cancer. In an aspect, disclosed compounds have utility in treating a gemcitabine-resistant pancreatic cancer.

In an aspect, the cell is mammalian, for example, human. In an aspect, the cell has been isolated from a subject prior to the contacting step. In an aspect, contacting is via administration to a subject. In aspect, modulation is inhibition of ANGPTL4 activity.

In an aspect, the disclosure pertains to a method for modulation of ANGPTL4 activity in a subject comprising the step of administering to the subject at least one disclosed compound or at least one product of a disclosed method in a dosage and amount effective to inhibit ANGPTL4 activity in the subject. In an aspect, the subject is mammalian, for example, human. In an aspect, the mammal has been diagnosed with a need for modulation of ANGPTL4 activity prior to the administering step. In an aspect, the mammal has been diagnosed with a need for modulation of ANGPTL4 activity prior to the administering step. In an aspect, the method further comprises the step of identifying a subject in need of modulation of ANGPTL4 activity.

In an aspect, the disclosure pertains to a method for the treatment of a cancer associated with an ANGPTL4 dysfunction, for example, a cancer associated with increased ANGPTL4 expression, in a mammal comprising the step of administering to the mammal at least one disclosed compound or at least one product of a disclosed method in a dosage and amount effective to treat the disorder in the mammal. In an aspect, the mammal is a human. In an aspect, the mammal has been diagnosed with a need for treatment for the disorder prior to the administering step. In an aspect, the method further comprises the step of identifying a subject in need of treatment for the disorder.

In an aspect, disclosed compounds can be used in combination with one or more other drugs in the treatment, prevention, control, amelioration, or reduction of risk of cancers or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, disclosed compounds and the other active ingredients can be used in lower doses than when each is used singly.

Disclosed methods comprise treating a subject with one or more other active ingredients, in addition to a disclosed compound of the present disclosure. For example, disclosed compounds can be coadministered in the disclosed methods with one or more additional drugs, such as a known anti-cancer drug. In an aspect, "coadministered" can be administration of a fixed dosage form combination drug comprising a disclosed compound and a known anti-cancer drug. In an aspect, "coadministered" can be administration of separate dosage forms, e.g., the disclosed compound as a solid oral dosage form and the anti-cancer drug as an intravenous dosage form. A disclosed compound and other active agents can be administered separately or in conjunction with each other. In addition, the administration of a disclosed compound can be prior to, concurrent to, or subsequent to the administration of another agent(s). A disclosed compound and the other agent can be coadministered, either in concomitant therapy or in a fixed combination.

In an aspect, a disclosed compound can be employed in combination with other known anticancer agents, and combinations thereof, and the like, or a disclosed compound can be administered in conjunction with the use of physical methods such as with radiation therapy or surgery.

In an aspect, disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In an aspect, disclosed compounds can be coadministered in the disclosed methods with a hormone therapy agent. In a still further aspect, the hormone therapy agent leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, or testolactone, or a pharmaceutically acceptable salt thereof, or combinations thereof.

In an aspect, disclosed compounds can be coadministered in the disclosed methods with a chemotherapeutic agent. In a still further aspect, the chemotherapeutic agent coadministered in the disclosed methods is selected from one or more of the group consisting of an alkylating-like agent, an antimetabolite agent, an antineoplastic antibiotic agent, a mitotic inhibitor agent, an mTor inhibitor agent or another chemotherapeutic agent, or combinations thereof.

In an aspect, disclosed compounds can be coadministered in the disclosed methods with an antineoplastic antibiotic agent such as doxorubicin, mitoxantrone, bleomycin, daunorubicin, dactinomycin, epirubicin, idarubicin, plicamycin, mitomycin, pentostatin, or valrubicin, or a pharmaceutically acceptable salt thereof, or combinations thereof.

In an aspect, disclosed compounds can be coadministered in the disclosed methods with an antimetabolite agent such as gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, or thioguanine, or a pharmaceutically acceptable salt thereof, or combinations thereof.

In an aspect, disclosed compounds can be coadministered in the disclosed methods with an alkylating-like agent such as carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, or streptozocin, or a pharmaceutically acceptable salt thereof, or combinations thereof.

In an aspect, disclosed compounds can be coadministered in the disclosed methods with a mitotic inhibitor agent such as etopside, vincristine, ixabepilone, vinorelbine, vinblastine, or teniposide, or a pharmaceutically acceptable salt thereof, or combinations thereof.

In an aspect, disclosed compounds can be coadministered in the disclosed methods with a mTor inhibitor agent such as everolimus, siroliumus, or temsirolimus, or a pharmaceutically acceptable salt thereof, or combinations thereof.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1;1000, preferably about 200:1 to about 1:200. Combinations of a compound of the present disclosure and other active ingredients will generally also be within the aforementioned range, but in each case, an effective dose of each active ingredient should be used.

In the treatment of conditions such as cancer, an appropriate dosage level can be about 0.01 to 500 mg per kg patient body weight per day which can be administered in single or multiple doses. Preferably, the dosage level can be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In an aspect of a disclosed method, the subject has been diagnosed with a need for treatment prior to the administering step. In an aspect of a disclosed method, the subject has been diagnosed with a disorder treatable by modulation of ANGPTL4 activity and/or a need for modulation of ANGPTL4 activity prior to the administering step. In an aspect of a disclosed method, the subject has been diagnosed with a disorder of uncontrolled cellular proliferation prior to the administering step. In an aspect, a subject can be treated prophylactically with a compound or composition disclosed herein.

In an aspect, the disclosure pertains to a medicament comprising one or more disclosed compounds; or a pharmaceutically acceptable salt thereof. In an aspect, the one or more compounds is a product of a disclosed method of making.

In various aspect, the disclosure pertains to methods for the manufacture of a medicament for modulation of ANGPTL4 activity (e.g., treatment of one or more disorders of uncontrolled cellular proliferation associated with an ANGPTL4 dysfunction) in mammals (e.g., humans) comprising combining one or more disclosed compounds, products, or compositions or a pharmaceutically acceptable salt thereof, with a pharmaceutically acceptable carrier. It is understood that the disclosed methods can be performed with disclosed compounds, products, and pharmaceutical compositions. It is also understood that the disclosed methods can be employed in connection with the disclosed methods of using.

Also provided are the uses of disclosed compounds and products. In an aspect, the disclosure pertains to use of at least one disclosed compound; or a pharmaceutically acceptable salt thereof. In an aspect, the compound used is a product of a disclosed method of making.

In an aspect, the compound used exhibits modulation of ANGPTL4 activity with an $IC_{50}$ of less than about 50 µM. In an aspect, the compound used exhibits modulation of ANGPTL4 activity with an $IC_{50}$ of less than about 25 µM. In an aspect, the compound used exhibits modulation of ANGPTL4 activity with an $IC_{50}$ of less than about 10 µM. In an aspect, the compound used exhibits modulation of ANGPTL4 activity with an $IC_{50}$ of less than about 5 µM. In an aspect, the compound used exhibits modulation of ANGPTL4 activity with an $IC_{50}$ of less than about 500 nM. In an aspect, the compound used exhibits modulation of ANGPTL4 activity with an $IC_{50}$ of less than about 250 nM. In an aspect, the compound used exhibits modulation of ANGPTL4 activity with an $IC_{50}$ of less than about 100 nM. In an aspect, the compound used exhibits modulation of ANGPTL4 activity with an $IC_{50}$ of less than about 50 nM.

In an aspect, the compound used exhibits modulation of ANGPTL4 activity with an $IC_{50}$ of less than about 10 nM.

In an aspect, the compound used exhibits modulation of ANGPTL4 activity with an $IC_{50}$ of between from about 1 nM to about 50 μM. In an aspect, the compound used exhibits modulation of ANGPTL4 activity with an $IC_{50}$ of between from about 1 nM to about 25 μM. In an aspect, the compound used exhibits modulation of ANGPTL4 activity with an $IC_{50}$ of between from about 1 nM to about 10 μM. In an aspect, the compound used exhibits modulation of ANGPTL4 activity with an $IC_{50}$ of between from about 1 nM to about 5 μM. In an aspect, the compound used exhibits modulation of ANGPTL4 activity with an $IC_{50}$ of between from about 1 nM to about 1 μM.

In an aspect, the compound used exhibits inhibition of cellular proliferation with an $IC_{50}$ of less than about 50 μM. In an aspect, the compound used exhibits inhibition of cellular proliferation with an $IC_{50}$ of less than about 25 μM. In an aspect, the compound used exhibits inhibition of cellular proliferation with an $IC_{50}$ of less than about 10 μM. In an aspect, the compound used exhibits inhibition of cellular proliferation with an $IC_{50}$ of less than about 5 μM. In an aspect, the compound used exhibits inhibition of cellular proliferation with an $IC_{50}$ of less than about 500 nM. In an aspect, the compound used exhibits inhibition of cellular proliferation with an $IC_{50}$ of less than about 250 nM. In an aspect, the compound used exhibits inhibition of cellular proliferation with an $IC_{50}$ of less than about 100 nM. In an aspect, the compound used exhibits inhibition of cellular proliferation with an $IC_{50}$ of less than about 50 nM. In an aspect, the compound used exhibits inhibition of cellular proliferation with an $IC_{50}$ of less than about 10 nM.

In an aspect, the compound used exhibits inhibition of cellular proliferation with an $IC_{50}$ of between from about 1 nM to about 50 μM. In an aspect, the compound used exhibits inhibition of cellular proliferation with an $IC_{50}$ of between from about 1 nM to about 25 μM. In an aspect, the compound used exhibits inhibition of cellular proliferation with an $IC_{50}$ of between from about 1 nM to about 10 μM. In an aspect, the compound used exhibits inhibition of cellular proliferation with an $IC_{50}$ of between from about 1 nM to about 5 μM. In an aspect, the compound used exhibits inhibition of cellular proliferation with an $IC_{50}$ of between from about 1 nM to about 1 μM.

In an aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In an aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder of uncontrolled cellular proliferation in a mammal. Also disclosed is the use of a compound for treatment of a cancer. In an aspect, the use is characterized in that the mammal is a human. In an aspect, the use is characterized in that the disorder is a disorder of uncontrolled cellular proliferation associated with an ANGPTL4 dysfunction. In an aspect, the disorder of uncontrolled cellular proliferation associated with an ANGPTL4 dysfunction can be treated by modulation of ANGPTL4 activity in a mammal.

In an aspect, the use relates to the manufacture of a medicament for the treatment of a disorder associated with ANGPTL4 activity in a mammal. In an aspect, the medicament is used in the treatment of a disorder of uncontrolled cellular proliferation associated with an ANGPTL4 dysfunction in a mammal.

In an aspect, the disclosure pertains to kits comprising at least one disclosed compound, or a pharmaceutically acceptable salt thereof, and at least one of: (a) at least one agent known to increase ANGPTL4 activity; (b) at least one agent known to decrease ANGPTL4 activity; (c) at least one agent known to treat a disorder associated with ANGPTL4 activity; (d) instructions for treating a disorder associated with ANGPTL4 activity; (e) instructions for treating a disorder associated with ANGPTL4 activity; or (f) instructions for administering the compound in connection with treating a disorder of uncontrolled cellular proliferation.

In an aspect, the disclosure pertains to kits comprising an effective amount of at least one compound having a structure represented by a formula:

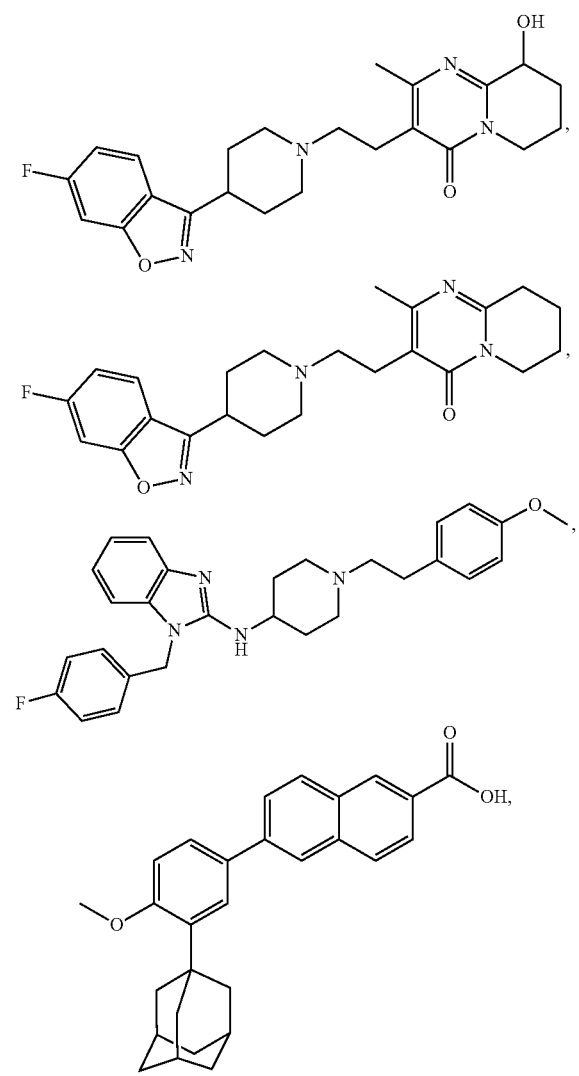

-continued

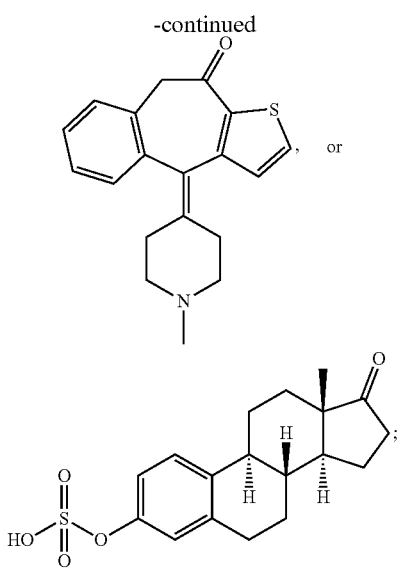

or a pharmaceutically acceptable salt thereof, and at least one of: (a) at least one agent known to increase ANGPTL4 activity; (b) at least one agent known to decrease ANGPTL4 activity; (c) at least one agent known to treat a disorder associated with ANGPTL4 activity; (d) instructions for treating a disorder associated with ANGPTL4 activity; (e) instructions for treating a disorder associated with ANGPTL4 activity; or (f) instructions for administering the compound in connection with treating a disorder of uncontrolled cellular proliferation.

In an aspect, the disclosure pertains to kits comprising at least one disclosed compound and at least one agent known to inhibit cellular proliferation.

In an aspect, the kit comprises a disclosed compound or a product of a disclosed method of making.

In an aspect, the at least one compound and the at least one agent are co-formulated. In an aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

In an aspect, the at least one agent is a hormone therapy agent. In an aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt thereof.

In an aspect, the at least one agent is a chemotherapeutic agent. In an aspect, the chemotherapeutic agent is selected from one or more of the group consisting of an alkylating-like agent, an antimetabolite agent, an antineoplastic antibiotic agent, a mitotic inhibitor agent, an mTor inhibitor agent or other chemotherapeutic agent.

In an aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In an aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In an aspect, the alkylating-like agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In an aspect, the mitotic inhibitor agent is selected from one or more of the group consisting of etoposide, vincristine, ixabepilone, vinorelbine, vinblastine, and teniposide, or a pharmaceutically acceptable salt thereof.

In an aspect, the mTor inhibitor agent is selected from one or more of the group consisting of everolimus, siroliumus, and temsirolimus, or a pharmaceutically acceptable salt thereof.

In an aspect, the kit further comprises instructions to provide the compound in connection with surgery. In an aspect, the kit further comprises instructions to provide the compound in connection with surgery, wherein the instructions provide that surgery is performed prior to the administering of at least one compound. In an aspect, the kit further comprises instructions to provide the compound in connection with surgery, wherein the instructions provide that surgery is performed after the administering of at least one compound. In an aspect, the kit further comprises instructions to provide the compound in connection with surgery, wherein the instructions provide that surgery is performed after the administering of at least one compound, and wherein the instructions provide that the administering of at least one compound is to effect presurgical debulking of a tumor. In an aspect, the kit further comprises instructions to provide the compound in connection with surgery, wherein the instructions provide that surgery is performed after the administering of at least one compound, and wherein the instructions provide that surgery is performed at about the same time as the administering of at least one compound.

In an aspect, the kit further comprises instructions to provide the compound in connection with radiotherapy. In an aspect, the kit further comprises instructions to provide the compound in connection with radiotherapy, wherein the instructions provide that radiotherapy is performed prior to the administering of at least one compound. In an aspect, the kit further comprises instructions to provide the compound in connection with radiotherapy, wherein the instructions provide that radiotherapy is performed after the step of the administering of at least one compound. In an aspect, the kit further comprises instructions to provide the compound in connection with radiotherapy, wherein the instructions provide that radiotherapy is performed at about the same time as the step of the administering of at least one compound.

In an aspect, the kit further comprises a plurality of dosage forms, the plurality comprising one or more doses; wherein each dose comprises a therapeutically effective amount of the compound and the at least one agent. In an aspect, the kit further comprises a plurality of dosage forms, the plurality comprising one or more doses; wherein each dose comprises a therapeutically effective amount of the compound and the at least one agent, and wherein each dose of the compound and the at least one agent are co-formulated. In an aspect, the kit further comprises a plurality of dosage forms, the plurality comprising one or more doses; wherein each dose comprises a therapeutically effective amount of the compound and the at least one agent, and wherein each dose of the compound and the at least one agent are co-packaged.

In an aspect, the kit further comprises a plurality of dosage forms, the plurality comprising one or more doses; wherein each dose comprises a therapeutically effective amount of the compound and the at least one agent, and wherein the dosage forms are formulated for oral administration and/or intravenous administration. In an aspect, the kit further comprises a plurality of dosage forms, the plurality comprising one or more doses; wherein each dose comprises a therapeutically effective amount of the compound and the at least one agent, and wherein the dosage forms are formulated for oral administration. In an aspect, the kit further comprises a plurality of dosage forms, the plurality comprising one or more doses; wherein each dose comprises a therapeutically effective amount of the compound and the at least one agent, and wherein the dosage forms are formulated for intravenous administration.

In an aspect, the kit further comprises a plurality of dosage forms, the plurality comprising one or more doses; wherein each dose comprises a therapeutically effective amount of the compound and the at least one agent; and wherein the dosage form for the compound is formulated for oral administration and the dosage form for the at least one agent is formulated for intravenous administration. In an aspect, the kit further comprises a plurality of dosage forms, the plurality comprising one or more doses; wherein each dose comprises a therapeutically effective amount of the compound and the at least one agent; and wherein the dosage form for the compound is formulated for intravenous administration and the dosage form for the at least one agent is formulated for oral administration.

In an aspect, the instructions for treating a disorder of uncontrolled cellular proliferation provide instructions for treating a cancer.

It is understood that the disclosed kits can be prepared from disclosed compounds, products, and pharmaceutical compositions. It is also understood that the disclosed kits can be employed in connection with the disclosed methods of using.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

In silico docking study of small molecule libraries with the cANGPTL4 protein structure. The protein structure (PDB ID: 5TCN) for a C-terminal fragment of ANGPTL4, designated cANGPTL4, was used to determine binding affinities of digital compound libraries. The software used was Autodock Vina 1.1.2 and SwissDock. The Zinc compound libraries in pdbqt format: NCI Diversity Set 2, Drug Bank Small Molecules, and FDA Approved Compound Set were used for the Autodock Vina docking study. The software was run on default settings except for the exhaustiveness setting, which was run at 8, 16, and 24. The top 20 compounds based on lowest binding energy (kcal/mol) were prioritized and docked with SwissDock. All of the data and visualization of binding poses in Pymol were considered in choosing the top nine compounds for in vitro screening, which are shown in Table I below.

TABLE I

| No. | Name | Binding Affinity (kca/mol) | | Structure |
| | | Vina Affinity | SwissDock Affinity | |
| --- | --- | --- | --- | --- |
| 1 | paliperidone | −10.5 | −8.98 | 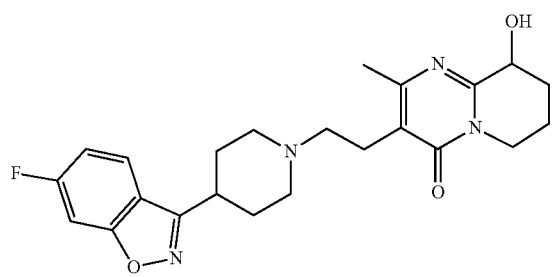 [SMILES: Cc1nc2n(c(=O)c1CCN1CCC(c3noc4cc(F)ccc34)CC1)CCCC2O] |

TABLE I-continued

| No. | Name | Vina Affinity | SwissDock Affinity | Structure |
|---|---|---|---|---|
| 2 | adapalene | −9.5 | −9.3 | 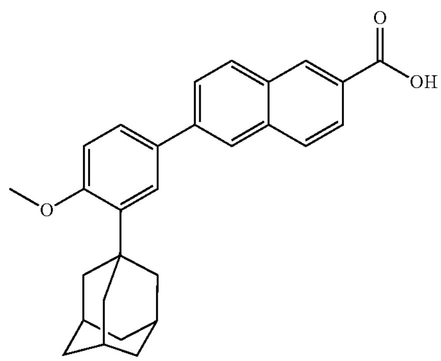 [SMILES: COc1ccc(-c2ccc3cc(C(=O)O)ccc3c2)cc1C12CC3CC(CC(C3)C1)C2] |
| 3 | ketotifen | −7.1 | −7.4 | 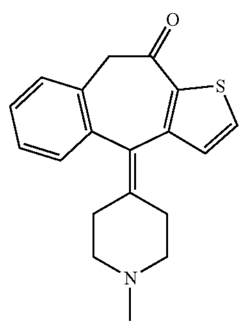 [SMILES: CN1CCC(=C2c3ccccc3CC(=O)c3sccc32)CC1] |
| 4 | estropipate | −7.5 | 7.8 | 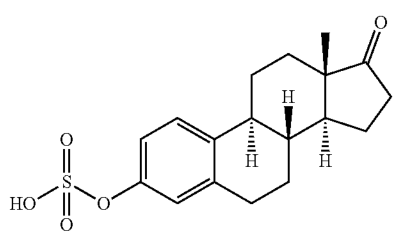 |
| 5 | bentiromide | −8.0 | −9.06 | 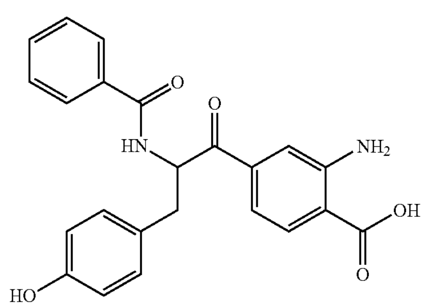 [SMILES: Nc1cc(C(=O)C(Cc2ccc(O)cc2)NC(=O)c2ccccc2)ccc1C(=O)O] |
| 6 | risperidone | −10.2 | −7.97 | 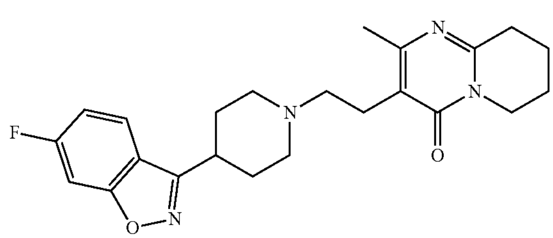 [SMILES: Cc1nc2n(c(=O)c1CCN1CCC(c3noc4cc(F)ccc34)CC1)CCCC2] |

Binding Affinity (kca/mol)

TABLE I-continued

| No. | Name | Binding Affinity (kca/mol) | | Structure |
|---|---|---|---|---|
| | | Vina Affinity | SwissDock Affinity | |
| 7 | desonide | −7.1 | −7.44 | 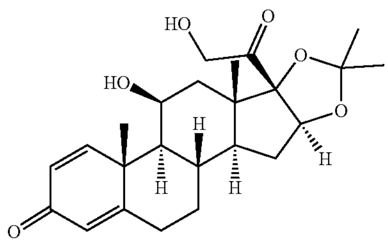 |
| 8 | glimepiride | −7.5 | — | 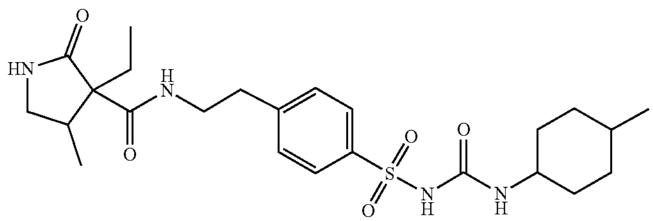 [SMILES: CCC1(C(=O)NCCc2ccc(S(=O)(=O)NC(=O)NC3CCC(C)CC3)cc2)C(=O)NCC1C] |
| 9 | astemizole | −8.6 | −8.14 | 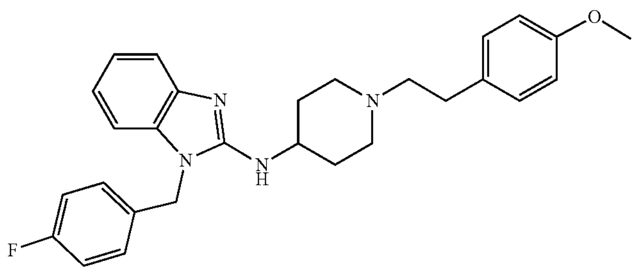 [SMILES: COc1ccc(CCN2CCC(Nc3nc4ccccc4n3Cc3ccc(F)cc3)CC2)cc1] |

The in vitro screening results (using the assay methods described below) for compound nos. (see Table I) 1, 2, 3, 4, 6, and 9 are shown in FIGS. 1, 8, 9, 10, 2, and 3, respectively. The in vitro screening results for compounds 5, 7, and 8 did not show any appreciable inhibition of cell-proliferation under similar assay conditions at the concentrations shown in FIGS. 1-3 and 8-10.

In vitro compound screening against pancreatic cancer cell lines for $IC_{50}$ determination. Cell Titer-Glo® luminescent cell viability assay (Promega, Wis., USA) was used to measure cytotoxicity at 24 and 48-hour post dosing with compounds 1-9 at 10 nM, 100 nM, 1 µM, 10 µM, and 100 µM concentrations (n=4). ASPC-1, BXPC-3, MIA-PaCa-2, and PANC-1 cell lines were obtained from ATCC. Representative data obtained using the assay for representative compounds are shown in FIGS. 1-3 and 8-10. The data show that the compounds effectively inhibit cellular proliferation. It should be noted that PANC-1, MIA-PaCa-2 and BxPC-3 cell-lines are gemcitabine-resistant cell-lines.

The $IC_{50}$ was calculated using the following Log (inhibitor) versus Response equation:

$$Y = \text{Bottom} + (\text{Top} - \text{Bottom})/(1 + 10\textasciicircum((X - \text{Log IC50}))).$$

Representative data and calculated $IC_{50}$ values using the assay for representative compounds are shown FIGS. 4-7.

Crystallization and ligand soaking. Crystallization was performed with fluorescently-labelled ANGPLT4 protein (labeled with carboxyrhodamine-succinimidyl ester) at a protein concentration of 12 mg/ml in 25 mM Bis-Tris-propane with 50 mM NaCl, pH 9.2. The sample was subsequently mixed with a precipitating solution (0.1M HEPES at pH 7.5, 0.1M sodium chloride, and 1.6M ammonium sulfate) in a 2:1, 1:1 and 1:2 volume ratio within a 3 ul droplet. The droplet was allowed to equilibrate against 100 µl of the precipitating solution by sitting drop vapor diffusion at room temperature. Prismatic crystals were formed within 3 days. Prior to X-ray data collection, the crystals were soaked in cryo-preserving solution containing the precipitating solution with a concentration of ~30% glycerol and 1 mM astemizole for about 2 minutes. The crystals were then immediately flashed-cooled in liquid nitrogen prior to diffraction analysis. Based upon the crystallographic data, models for binding of astemizole were developed and the results are shown in FIGS. 11A-12B.

Pharmaceutical Composition Examples. "Active ingredient" as used throughout these examples relates to one or more disclosed compounds or products of disclosed methods of making as described hereinbefore, or a pharmaceutically acceptable salt thereof. The following examples of the formulation of the compounds of the present disclosure in tablets, suspension, injectables and ointments are prophetic. Typical examples of recipes for the formulation of the disclosure are as given below.

Various other dosage forms can be applied herein such as a filled gelatin capsule, liquid emulsion/suspension, ointments, suppositories or chewable tablet form employing disclosed compounds in desired dosage amounts in accordance with the present disclosure. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

A tablet can be prepared as follows:

| A tablet can be prepared as follows: | |
| --- | --- |
| Component | Amount |
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is molded using a customary tablet press (e.g. tablet format: diameter 8 mm, curvature radius 12 mm). The molding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present disclosure, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

A parenteral composition can be prepared as follows:

| A parenteral composition can be prepared as follows: | |
| --- | --- |
| Component | Amount |
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 µm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this Example, active ingredient can be replaced with the same amount of any of the compounds according to the present disclosure, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

In silico docking study of small molecule libraries with the cANGPTL4 protein structure. Additional in silico docking studies were carried out as described herein above. Compounds identified in these studies and subject to the disclosure and claims of the present application are described below in Table 2.

TABLE 2
| Class | Structure | Binding energy Kcal/mol | Swiss Dock |
|---|---|---|---|
| Others | 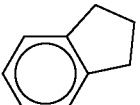 | −11.6 | −1101.90 |
| Substituted phenyl | 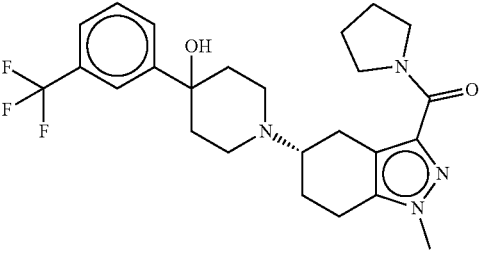 | −11.2 | −1127.25 |
| Naphthalene | 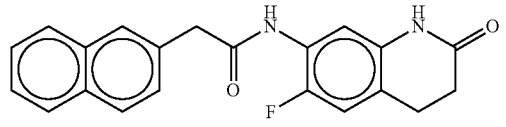 | −11.5 | −1131.99 |
| Benzo-dioxo | 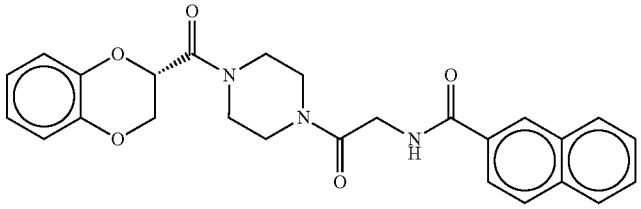 | −11.4 | −1051.98 |
|  | 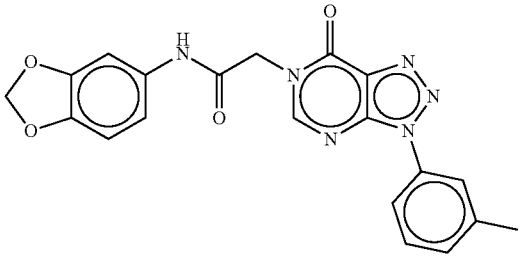 | −11.4 | −1095.29 |
| quinazoline | 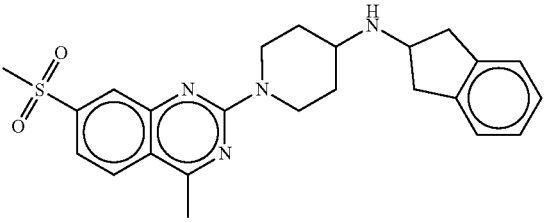 | −11.4 | −1180.93 |
| Dihydroquinoline | 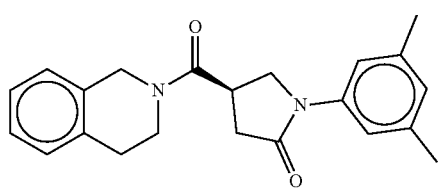 | −11.3 | −1149.18 |

TABLE 2-continued

| Class | Structure | Binding energy Kcal/mol | Swiss Dock |
|---|---|---|---|
| Alkyl phenyl | 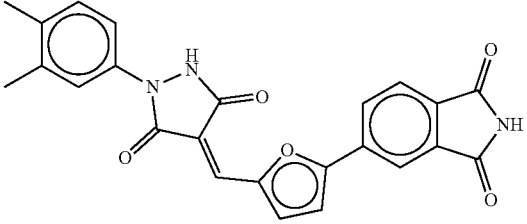 | −11.4 | −1135.29 |
| | 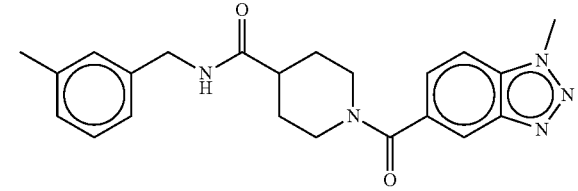 | −11.3 | −1154.72 |
| Phenyl | 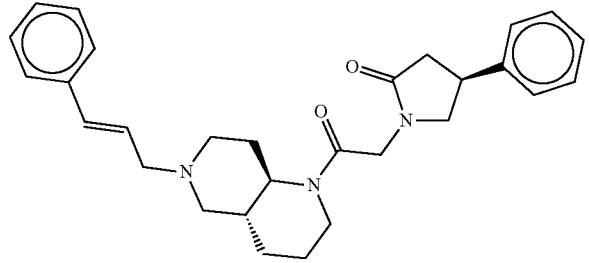 | −11 | −1160.52 |

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of treating pancreatic cancer in a mammal comprising the step of administering to the mammal a therapeutically effective amount of compound of formula

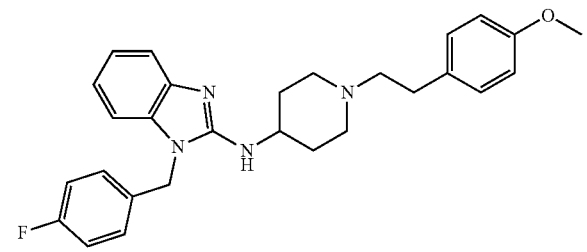 [SMILES: COc1ccc(CCN2CCC(Nc3nc4ccccc4n3Cc3ccc(F)cc3)CC2)cc1]

or a pharmaceutically acceptable salt thereof.

2. The method of claim 1, wherein the pancreatic cancer is a gemcitabine-resistant pancreatic cancer.

* * * * *